United States Patent [19]

Shultz et al.

[11] Patent Number: 5,705,649

[45] Date of Patent: Jan. 6, 1998

[54] PROTEIN STAINING COMPOSITIONS AND METHODS

[75] Inventors: John W. Shultz; David L. Leland, both of Verona, Wis.

[73] Assignee: Promega Corporation, Madison, Wis.

[21] Appl. No.: 555,614

[22] Filed: Nov. 9, 1995

Related U.S. Application Data

[60] Division of Ser. No. 70,512, Jun. 1, 1993, abandoned, which is a continuation-in-part of Ser. No. 916,539, Jul. 20, 1992, Pat. No. 5,273,906.

[51] Int. Cl.$^6$ .................................................. C07D 271/12
[52] U.S. Cl. ........................................... 548/125; 436/86
[58] Field of Search ............................... 548/126; 436/86

[56] References Cited

U.S. PATENT DOCUMENTS

| | | |
|---|---|---|
| 2,055,607 | 9/1936 | Linch et al. . |
| 2,085,736 | 7/1937 | Calcott et al. . |
| 4,023,933 | 5/1977 | Bradford et al. . |
| 4,219,337 | 8/1980 | Grossberg et al. . |
| 4,474,691 | 10/1984 | Schindler ............................... 548/126 |
| 4,966,854 | 10/1990 | Fleming . |
| 5,013,857 | 5/1991 | Berneth et al. . |
| 5,101,020 | 3/1992 | Fleming . |

FOREIGN PATENT DOCUMENTS

| | | |
|---|---|---|
| 253271 | 1/1988 | European Pat. Off. . |
| 2914299 | 10/1980 | Germany . |
| 4018080 | 1/1992 | Japan . |
| 159907 | 1/1964 | U.S.S.R. . |

OTHER PUBLICATIONS

MacPhee, Chem.–Biol. Interact 19(1)77 1977 Abstract.

Michael W. Hunkapiller, et al., "Isolation of Microgram Quantities of Proteins from Polyacrylamide Gels for Amino Acid Sequence Analysis", Methods in Enzymology, vol. 91, No. 17, 1983, pp. 227–236.

Curtis M. Wilson, "Staining of Proteins on Gels: Comparisons of Dyes and Procedures", Methods in Enzymology, vol. 91, No. 18, 1983, pp. 236–247.

Millipore Corp., "Direct Protein Microsequencing from the Immobilon™ Transfer Membrane", Immobilon™ Tech Protocol (1987).

H. Schägger, et al., "Coomassie Blue–Sodium Dodecyl Sulfate–Polyacrylamide Gel Electrophoresis for Direct Visualization of Polypeptides during Electrophoresis," Anal. Biochem 173, pp. 201–205 (1988).

B.D. Hames, "Peptide Mapping by Limited Proteolysis Using SDS–Polyacrylamide Gel Electrophoresis," Gel Electrophoresis of Proteins–a Practical Approach, B. Hames and D. Rickwood, eds., IRL Press, Washington, D.C. (1989), pp. 219–228.

B. Zehr, et al., "A One–Step, Low Background Coomassie Staining Procedure for Polyacrylamide Gels," Anal. Biochem, vol. 182, pp. 157–159 (1989).

*Primary Examiner*—Robert Gerstl
*Attorney, Agent, or Firm*—Foley & Lardner

[57] ABSTRACT

The present invention provides novel dyes for staining proteins, particularly those in electrophoretic gels, and detecting the proteins with high sensitivity. The dyes of the invention are derivatives of known dyes that are more hydrophobic than the corresponding, known dyes and, in electrophoretic gels, including polyacrylamide gels with sodium dodecyl sulfate, form easily detectable, non-covalent complexes with proteins. In some cases, the corresponding, known dyes bind to protein covalently. The complexes of protein with some dyes of the invention can be detected with high sensitivity simply by observation of the color of the complexes by eye. The complexes of protein with other dyes of the invention are detected by observation of the fluorescence of the complexes. Dyes of the invention include derivatives of Coomassie® dyes, acid blue 25, dansyl chloride, fluorescein, 2-methyl-2,4-diphenyl-3(2H)-furanone, and (7-nitrobenz-2-oxa-1,3-diazol-4-yl)amino alkanoates. The invention also provides quantitative and qualitative methods for detecting proteins which comprise staining the proteins with a dye of the invention.

6 Claims, No Drawings

PROTEIN STAINING COMPOSITIONS AND METHODS

RELATED APPLICATION

This is a division of application Ser. No. 070,512, filed Jun. 1, 1993 now abandoned which is a cip of Ser. No. 916,539 filed Jul. 20, 1992, now U.S. Pat. No. 5,273,906.

TECHNICAL FIELD

The present invention relates to the detection of proteins using synthetic dyes. More specifically, it relates to novel dyes and novel, improved methods of using the dyes for the detection and quantitation of proteins, particularly during electrophoretic separations.

BACKGROUND OF THE INVENTION

The most powerful and widely used method for the analysis of proteins is the separation of proteins in inert supports by the application of an electric field across the support which causes the proteins in the sample to migrate in a predictable and reproducible manner. See, e.g., Gel Electrophoresis of Proteins: A Practical Approach edited by Hames, B. and Rickwood, D., IRL Press, Washington D.C. (1989). In general, the supports are made from polymers such as polyacrylamide—a polymer of acrylamide and bisacrylamide- or agarose—a polymer of glucose units. Commonly, the separation of the protein sample is performed without the advantage of visualizing the separate components as they fractionate and then, after the separation, the components are detected by staining the constituents by the use of colored dyes. Such dyes include amido black and Coomassie® dyes, such as Coomassie Brilliant Blue G-250® dye (Color Index No. 42655) (referred to hereinafter as Coomassie Blue G-250) or Coomassie Brilliant Blue R-250® dye (Color Index No. 42660) (referred to hereinafter as Coomassie Blue R-250). Such staining agents are needed to detect the proteins, for almost all proteins are transparent in solution, polyacrylamide or agarose gels, or other inert supports and thus cannot be detected visually. The staining of the proteins is normally accomplished by soaking the support containing the separated sample in a solution of the stain, which impregnates the support completely, followed by the removal of the stain from the regions of the support not containing protein by such means as passive diffusion or electrophoresis. The maximal sensitivity for detection of any protein depends on the affinity of the dye for the protein and the extinction coefficient of the dye-protein complex. However, the smallest detectable levels of protein in an inert support, such as a polyacrylamide or agarose gel, is usually determined after the level of dye in the regions of the support not containing protein is reduced to the lowest possible level, thus allowing the largest visual difference between the stained protein and the support.

By far, the most widely used and accepted variants of the electrophoretic fractionation methods described above are separations of sodium dodecyl sulfate (SDS)-coated proteins in a support of polyacrylamide or agarose. Such methodology has been widely used to, among other things, determine the purity of protein samples; monitor the reaction of proteins with various agents; separate protein samples or segments of a single protein for subsequent immunological, radiological or protein-sequence analysis; and compare the relatedness of proteins by various analytical methods. This separation methodology, usually abbreviated SDS-PAGE when polyacrylamide gel electrophoresis has been used, has also been employed for the isolation of small amounts of pure protein for various end uses, such as diagnostic or therapeutic applications. Detection of the separated proteins on a SDS-PAGE or SDS-agarose gel is commonly done by exposing the gel, and concomitantly staining the protein bands, with a dye, such as a Coomassie Blue dye, as indicated above. In fact, Coomassie Blue dyes, which are also known by other names such as Serva Blue, Brilliant Blue, Cyanin, Indocyanin, and Eriosin Brilliant Cyanin, as well as others, are most commonly used due to their ease of use and great sensitivity in the detection of very small amounts of protein. See Wilson, C., Meth. Enzymol. 91, 236–247 (1983).

Practitioners in the art have combined the resolving power of SDS-PAGE and SDS-agarose gel electrophoresis with other techniques, such as isoelectric focusing of proteins in various inert supports, to provide some powerful fractionation techniques. These techniques, usually referred to as two-dimensional gel electrophoresis (2-D gel electrophoresis) techniques, are normally performed by a first fractionation of the sample on a polyacrylamide or agarose support by virtue of the intrinsic charges on the proteins followed by second fractionation of the separated polypeptide chains in a direction perpendicular to the direction of the first fractionation after coating of the protein sample with SDS. Hames, B. and Rickwood, D. supra. Such techniques are claimed to be capable of separating 5,000 to 10,000 protein components simultaneously, thus making them the most powerful separation methods available. Again, detection of the proteins in the fractionated sample is done by staining of the support after the fractionations by a stain such as Coomassie Blue dye.

In certain procedures, care is taken to preserve the intrinsic enzymatic and structural properties of the protein components in the sample while performing PAGE or agarose gel electrophoresis. Such gels, known as native gels, then allow the detection of some of the separated proteins by virtue of their activities (e.g., enzymatic activities).

The amounts of the individual protein constituents present in samples fractionated on SDS-PAGE gels can be determined by measurement of the amount of dye bound to the protein bands by densitometry or, following elution of the bound dye, by direct absorption methods.

However, as powerful as the techniques like those described above are, there are several disadvantages inherent in them that limit their use.

While various staining agents such as Coomassie Blue dyes can be used to stain proteins in SDS-PAGE and native-PAGE gels, the staining process takes considerable time, exposes the sample to undesirable conditions (such as acidic pH or the presence of organic solvents), and has been reported to entrap, "fix", proteins in the support. Zehr, B. et al., "A One-step, Low Background Coomassie Staining Procedure for Polyacrylamide Gels," Analyt. Biochem., 182: 157–159(1989); Wilson, C., "Staining of Proteins on Gels: Comparisons of Dyes and Procedures," Methods in Enzymology, supra. Some researchers have tried to circumvent these difficulties by adding the stain to the separation matrix prior to the separation; however such procedures result in stain levels present in the support matrix that make detection of low levels of protein impossible due to the color they give the support. Schragger et al., Anal. Biochem. 173, 201–205 (1988). Other scientists have used other chemical reagents such as ones that allow the detection of lipoproteins in gel supports. However, these methods do not render detectable the majority of proteins and thus are of very limited use. What is needed, then, are general stains (i.e., dyes) that can be used to provide detectability to all or almost all of the protein in a support without deeply coloring the support.

While some protein components can be identified in native gels, many proteins cannot be easily detected in this way because presence of the protein in a support matrix complicates or prevents detection via structural, enzymatic or other attributes of proteins. Again, what is needed to improve such methods are dyes that can be used to provide detectability to a protein in such a matrix without relying on the protein's intrinsic structural or enzymatic properties or other intrinsic characteristics that could provide detectability.

While protein can be quantitated in gels with great sensitivity by the use of densitometry and related methods, these procedures require that the dye in the gel matrix be substantially completely removed from the areas of the gel not containing protein. This can take a very long time under some circumstances or can require the use of expensive electrical destaining equipment made for this purpose. What is needed are dyes that can be used to quickly and sensitively detect protein in gel supports yet be rapidly removed, or not require removal at all, from the regions of the support not containing protein.

Finally, another drawback with some dyes, including unmodified Coomassie Blue dyes, is the need for very acidic conditions when the dye is used to quantitate protein in solution. Grossberg et al., U.S. Pat. No. 4,219,337; Bradford et al., U.S. Pat. No. 4,023,933. Because some proteins are insoluble under such conditions, they would not be capable of being measured accurately by such methods. Thus, dyes that can be used to quantitate protein under milder pH conditions would be advantageous.

With reference to Coomassie Blue dyes and derivatives thereof, see also Lillie, Conn's Biological Stains, 9th Ed., Williams & Wilkins Co., Baltimore, Md., USA (1977) and Fleming, U.S. Pat. No. 4,966,854.

Very sensitive detection of protein in gels can be accomplished if the protein, prior to application to the gel, is modified by addition of a fluorescent dye or stain ("tag") such as dansyl chloride, fluorescein isothiocyanate, or fluorescamine (see, e.g., Hames, B., in Chapter 1 in Gel Electrophoresis of Proteins: a Practical Approach, supra). Unfortunately, these methods entail covalent modification of protein and thus prevent use of the protein, after gel separation, in a number of applications, such as protein sequence analysis or use of the protein as an enzyme, if it is an enzyme in its native state. In addition, because such covalently binding dyes or stains attach to proteins through functional groups of amino acids, such as the epsilon amino groups of lysines or the alpha amino group of the amino-terminal amino acid, the dyes or stains do not detect all proteins with approximately the same sensitivity equally but, rather, stain differentially on the basis of the amino acid compositions of the proteins in question and thereby provide detectability with sensitivity that may vary widely from protein to protein in a sample. Therefore, techniques involving covalent binding of dyes or stains to proteins are not widely used in protein isolation or analysis. It would be advantageous to have available, in place of dyes and stains that bind covalently to proteins, derivatives that form non-covalent complexes with proteins in gels and other media, and thereby will typically stain different proteins to approximately the same extent, but that provide sensitivity in protein detection that is similar to that provided by the covalently binding.

SUMMARY OF THE INVENTION

The aforementioned needs in the art for improved dyes for staining proteins, through formation of non-covalent complexes, particularly in applications involving electrophoretic or other separations of proteins through inert supports, are addressed by the present invention. The invention also provides novel and improved methods for detecting proteins.

The present invention provides novel dyes that bind non-covalently to proteins with high affinity, in aqueous solution and in inert support materials such as polyacrylamide or agarose gels with or without detergent materials such as sodium dodecyl sulfate, to form non-covalent complexes that can be detected with high sensitivity on account of either color (i.e., absorption of light of wavelength in the visible range, that can be detected either visually (by the human eye) or spectrophotometrically) or fluorescence (i.e., fluorescent emission of light of wavelength in the visible range) of the complexed dye.

The dyes of the invention are derivatives of protein-staining dyes known in the prior art. The dyes of the invention have two functional regions: (1) a binding region, which is typically an hydrophobic, aliphatic or aromatic hydrocarbon segment and provides high affinity, non-covalent binding of the dye to protein and (2) a signalling region, which provides detectability with high sensitivity through either color or fluorescence.

A dye of the invention can be made by reacting a protein-staining dye known in the prior art with a suitable reagent to add, or increase the hydrophobicity of, an hydrophobic binding region but preserve a signalling region. If the prior art dye has a functional group, though which the dye binds protein covalently, the process of making a dye of the invention corresponding to the prior art dye modifies or eliminates the functional group so that the dye of the invention binds to protein only non-covalently.

We have discovered surprisingly that simply increasing the hydrophobicity of a prior-art, protein-staining dye, such as by adding a 6-15 carbon atom aliphatic chain, and, if necessary, eliminating the ability of the prior-art dye to bind protein covalently, provides a dye (an "enhanced hydrophobicity dye") which can be used in the improved methods of the invention for detecting proteins. Many enhanced hydrophobicity dyes are novel, and those that are novel are part of the present invention.

One improved method of the invention for detecting a protein comprises forming a complex of the protein with an enhanced hydrophobicity dye and then detecting the color of the dye-protein complex, visually or spectrophotometrically, if the complex is colored, or detecting the fluorescence of the dye-protein complex, if the complex is fluorescent. By the use of a transilluminator apparatus, well known to the skilled, visual detection of fluorescence can be facilitated.

Another improved method of the invention for detecting a protein in a sample comprises applying a sample solution comprising the protein to an inert support, such as a polyacrylamide or agarose gel, which may include a denaturant such as sodium dodecyl sulfate; separating the sample into protein fractions using electrophoresis; staining the protein on the support with an enhanced hydrophobicity dye, and detecting the stained protein visually or spectrophotometrically, if the dye of the stained protein is colored, or detecting the fluorescence of the stained protein, if the dye of the stained protein is fluorescent. Of course, a fluorescent dye may also be colored and a protein stained with such a dye of the invention may be detectable through its color as well as its fluorescence.

The detection methods of the invention may also comprise quantitation of one or more proteins in a protein sample.

Among its embodiments, the invention relates to "Coomassie" dye derivatives, which are of Formula XI

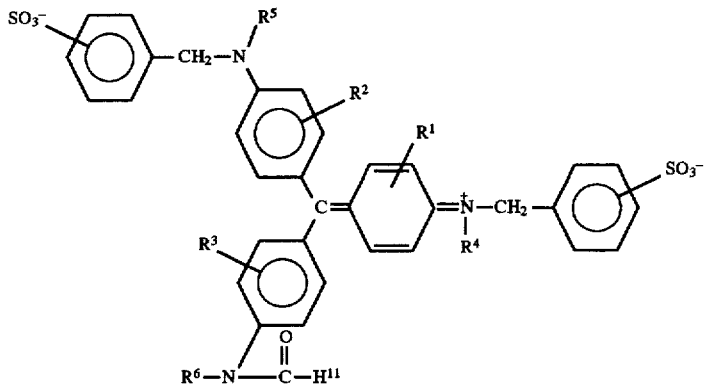

wherein an hydrophobic group, $H^{11}$, selected from the group consisting of substituted and unsubstituted alkyl, substituted and unsubstituted aryl, and substituted and unsubstituted arylalkyl groups, is bonded at the carbonyl of the —$R^6N$(C=O)— group and wherein $R^1$, $R^2$, and $R^3$ are independently selected from the group consisting of hydrogen, substituted and unsubstituted alkyl and substituted and unsubstituted aryl groups; $R^4$ and $R^5$ are independently selected from the group consisting of substituted and unsubstituted alkyl and substituted and unsubstituted aryl groups; $R^6$ is selected from the group consisting of hydrogen, substituted and unsubstituted alkyl, substituted and unsubstituted aryl, and substituted and unsubstituted arylalkyl groups. If the hydrophobic group, $H^{11}$, includes an activated —(C=O)— group (e.g., an activated ester or a —(C=O)Cl group), the activated —(C=O)— group may react with a second underivatized Coomassie molecule at the $R^6NH$— group thereof, such that a single hydrophobic group links two moieties of Formula XI (which may be the same or different). The invention also relates to salts of the derivatized Coomassie dyes, such as the sodium salt.

With reference to Formula XI, in a typical, underivatized (sometimes referred to herein as "unmodified") "Coomassie" dye, or salt thereof, such as the sodium salt, $R^1$ and $R^2$ are independently hydrogen or methyl, $R^3$ is hydrogen, $R^4$ and $R^5$ are ethyl, $R^6$ is phenyl or ethoxyphenyl, and there is an hydrogen in place of an acyl group at the nitrogen to which the $R^6$ group is bonded. The unmodified Coomassie dyes most widely used in the art are Coomassie Brilliant Blue G-250, also referred to as "Coomassie Blue G," in which, with reference to Formula XI, $R^2$ and $R^3$ are methyl and $R^6$ is ethoxyphenyl; and Coomassie Brilliant Blue R-250, also referred to as "Coomassie Blue R," in which, with reference to Formula XI, $R^2$ and $R^3$ are hydrogen and $R^6$ is ethoxyphenyl. The most commonly employed salt of the unmodified Coomassie dyes is the sodium salt.

Among other embodiments, the invention relates to "Acid Blue 25" derivatives, which are of Formula XII

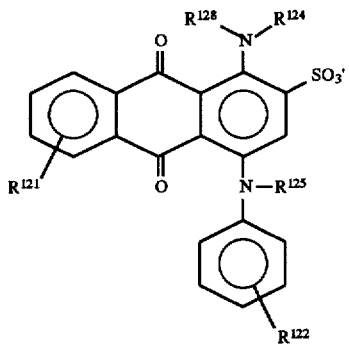

wherein $R^{124}$ is, independently of $R^{121}$, $R^{122}$, $R^{123}$, and $R^{125}$, —(C=O)$H^{124}$ or a group selected from the group consisting of hydrogen, substituted and unsubstituted alkyl, and substituted and unsubstituted aryl groups, $R^{125}$ is, independently of $R^{121}$, $R^{122}$, $R^{123}$, and $R^{124}$, —(C=O)$H^{125}$ or a group selected from the group consisting of hydrogen, substituted and unsubstituted alkyl, $H^{124}$ and $H^{125}$ are hydrophobic groups selected, independently for each of $R^{124}$ and $R^{125}$ if both $R^{124}$ is —(C=O)$H^{124}$ and $R^{125}$ is —(C=O)$H^{125}$, from the group consisting of substituted and unsubstituted alkyl, substituted and unsubstituted aryl, and substituted and unsubstituted arylalkyl groups, either $R^{124}$ is —(C=O)$H^{124}$ or $R^{125}$ is —(C=O)$H^{125}$ or both $R^{124}$ is —(C=O)$H^{124}$ and $R^{125}$ is —(C=O)$H^{125}$; $R^{121}$, $R^{122}$, $R^{123}$ are independently selected from the group consisting of hydrogen, substituted and unsubstituted alkyl, and substituted and unsubstituted aryl groups. If the $H^{124}$ or $H^{125}$ group includes an activated —(C=O)— group (e.g., an activated ester or a —(C=O)Cl group), the activated —(C=O)— group may react with a second underivatized Acid Blue 25 molecule, at an amino or substituted amino group thereof, such that a single hydrophobic group links two moieties of Formula XII (which may be the same or different). Alternatively, if the $H^{124}$ or $H^{125}$ group includes an activated —(C=O)— group, the activated —(C=O)— group may react with an amino or substituted amino group of the same molecule, such that a single hydrophobic group links the two amido groups of a moiety of Formula XII. The invention also relates to salts of the derivatized Acid Blue 25 dyes, such as the sodium or ammonium salt.

With reference to Formula XII, in a typical, underivatized or unmodified "Acid Blue 25" dye, or salt thereof, such as the sodium salt, $R^{121}$, $R^{122}$, $R^{123}$, $R^{124}$ and $R^{125}$ are all hydrogen. This is the case in "Acid Blue 25" itself.

In still other embodiments, the invention relates to fluorescein derivatives of Formula XIIIA

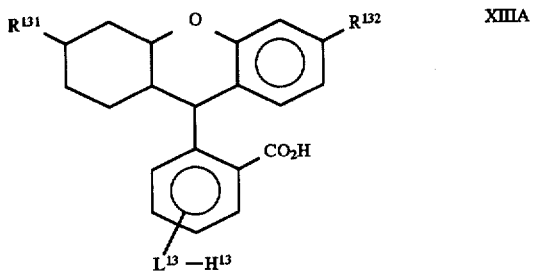

XIIIA wherein —$L^{13}$— is a linking moiety that joins hydrophobic group —$H^{13}$ to the phenyl group bearing the —$CO_2H$ moiety. The moiety —$L^{13}H^{13}$ is para to the —$CO_2H$ moiety (in the type II isomers) or meta to the —$CO_2H$ moiety (in the more preferred, type I isomers). Numerous fluorescein derivatives are available in the art to provide convenient linking groups, $L^{13}$, to which hydrophobic groups, $H^{13}$, selected from the group consisting of substituted and unsubstituted alkyl, substituted and unsubstituted aryl, and substituted and unsubstituted arylalkyl groups, are conveniently joined. Among these fluorescein derivatives are 5- (i.e., type I) or 6- (i.e., type II) carboxyfluorescein, succinimidyl ester, which can be reacted with compounds of formula $H_2NH^{13}$ to provide a dye of the invention of Formula XIIIA wherein $L^{13}$ is of formula —(C=O)(NH)—; 5-(bromoethyl) fluorescein, which can be reacted with a compound of formula $HSH^{13}$ to provide a dye of the invention wherein the linking group is of formula —$CH_2S$—; fluorescein-5-maleimide, which can be reacted with a compound of formula $HSH^{13}$ to provide a dye of the invention wherein the linking group is —S—; 5-iodoacetamidofluorescein, which can be reacted with a compound of formula $HSH^{13}$ to provide a dye of the invention wherein the linking group is of formula —NH(C=O)$CH_2S$—; 5-fluorescein sulfonylchloride or 6-sulfonylsulfonylchloride, which can be reacted with a compound of formula $H_2NH^{13}$ to provide a dye of the invention wherein $L^{13}$ is of formula —($SO_2$)NH—; and 5-isothiocyanatofluorescein or 6-isothiocyanatofluorescein, which can be reacted as described hereinbelow to provide a dye of the invention wherein the linking group is of formula —NH(C=S)NH—. Most preferred are the dyes made with the 5-isothiocyanatofluorescein.

Thus, the invention relates to "fluorescein thiourea" derivatives, which may also be regarded as "fluorescein isothiocyanate" derivatives and which are of Formula XIII

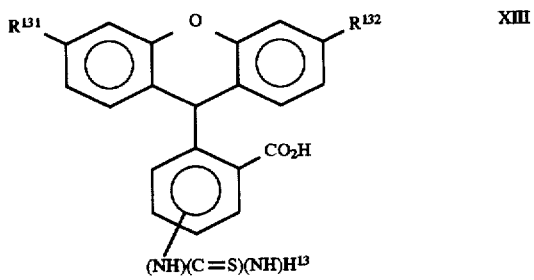

XIII wherein the hydrophobic group —$H^{13}$, defined as above, is bonded to the "thiourea" moiety, —NH(C=S)NH—. The —(NH)(C=S)(NH)— moiety is para or meta to the —$CO_2H$ moiety (isomer II or isomer I, respectively). As the skilled will understand, with reference to both Formula XIII and other structural formulas herein for compounds with a plurality of tautomers, the formula, unless specifically noted otherwise in a particular instance, is meant to represent all of the various tautomeric forms of the molecule even though the formula specifically depicts only one form. If the hydrophobic group bonded to the thiourea moiety includes a primary amino group, the primary amino group may react with a second underivatized fluorescein isothiocyanate molecule at the isothiocyanato group, such that a single hydrophobic group links two fluorescein thiourea moieties (which may be the same or different).

In both formula XIIIA and formula XIII, $R^{131}$ is selected from the group consisting of —OH and

wherein $R^{133}$ and $R^{134}$ are independently selected from alkyl groups, $R^{132}$ is oxygen if $R^{131}$ is —OH and

if $R^{132}$ is

The invention also relates to salts of the dyes which are fluorescein derivatives, such as the disodium salt, if $R^{131}$ is —OH (O⁻ in the salt), or the chloride salt, if $R^{131}$ is

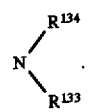

With reference to Formula XIII, in a typical, underivatized or unmodified fluorescein isothiocyanate dye, or salt thereof, such as the disodium or chloride salt, the thiourea moiety would be replaced with an isothiocyanato moiety, and $R^{131}$ would be —OH, —N($C_2H_5$)$_2$ (rhodamine B isothiocyanate), or —N($CH_3$)$_2$ (tetramethylrhodamine isothiocyanate). Underivatized fluorescein isothiocyanate dyes react with proteins to form covalent, thiourea linkages at free amino groups.

In another embodiment, the invention relates to "dansyl" derivatives, which are of Formula XIV

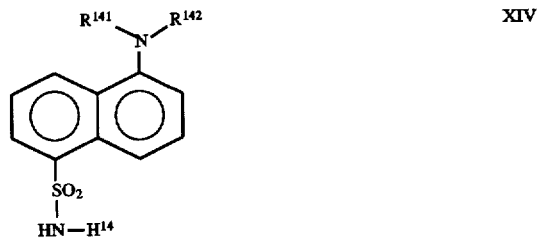

XIV wherein, to the nitrogen of the sulfonamido group, an hydrophobic group, $H^{14}$, selected from the group consisting of substituted and unsubstituted alkyl, substituted and unsubstituted aryl, and substituted and unsubstituted arylalkyl groups, is bonded. If the $H^{14}$ group includes a primary amino group, the primary amino group may react with a second underivatized dansyl molecule, at the nitrogen of the sulfonamido group, such that a single hydrophobic group links two dansyl moieties (which may be the same or different). $R^{141}$ and $R^{142}$ are independently selected from the group consisting of substituted and unsubstituted alkyl and substituted and unsubstituted aryl groups. The invention also relates to salts of the dansyl derivatives, such as the hydrochloride acid addition salt.

With reference to Formula XIV, in a typical, underivatized or unmodified dansyl dye, or salt thereof, such as the hydrochloride acid addition salt, $R^{141}$ and $R^{142}$ are the same and typically unsubstituted alkyl of 1 to 4 carbons, most typically methyl, and the sulfonamido group is a sulfonyl halide, usually the chloride. The well known dansyl chloride is 5-(dimethylamino)-1-naphthalenesulfonyl chloride. An underivatized dye reacts with protein to form covalent, sulfonamido linkages with free amino groups.

In still another embodiment, the invention relates to "MDPF" derivatives, which are of Formula XV

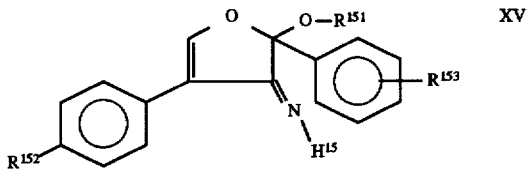

wherein, to the =N—, an hydrophobic group, $H^{15}$, selected from the group consisting of substituted and unsubstituted alkyl, substituted and unsubstituted aryl, and substituted and unsubstituted arylalkyl groups, is bonded. "MDPF" refers to "2-methoxy-2,4-diphenyl-3(2H)-furanone." If the $H^{15}$ group bonded to the =N— includes a primary amino group, the primary amino group may react with a second underivatized MDPF molecule, at the carbon of the keto group at the 3-position in the furan ring, such that a single hydrophobic group links two moieties (which may be the same or different) of Formula XV. $R^{151}$ is selected from the group consisting of substituted and unsubstituted alkyl and substituted and unsubstituted aryl groups. $R^{152}$ and $R^{153}$ are independently selected from the group consisting of hydrogen, substituted and unsubstituted alkyl and substituted and unsubstituted aryl groups. For MDPF derivatives which are capable of forming salts, e.g., acid addition salts due to the presence of a substituted amino group, the invention also relates to such salts.

With reference to Formula XV, in a typical, underivatized or unmodified MDPF dye, $R^{151}$ is unsubstituted alkyl, most typically methyl, $R^{152}$ and $R^{153}$ are both hydrogen, and =N— is replaced with =O at the 3-position of the furan ring. With reference to Formula XV, in MDPF itself, $R^{151}$ is methyl and $R^{152}$ and $R^{153}$ are both hydrogen. An underivatized MDPF dye reacts with protein to form covalent, Shiff base linkages with free amino groups.

DETAILED DESCRIPTION OF THE INVENTION

The present invention is directed to novel dyes and novel methods of using such dyes in the detection, analysis and quantitation of proteins The invention relates to protein-staining dyes, that have one or more polar functional groups, such as a primary or secondary amino group, a carboxyl group, a sulfonyl group, or an isothiocyanato group, that can be modified to yield a modified or "derivatized" dye that is more hydrophobic. Some of these (underivatized) dyes, through such a polar functional group, may bind covalently with protein. Thus, the novel dyes of the invention, and the dyes employed in the methods of the invention, are "enhanced hydrophobicity" dyes. These enhanced hydrophobicity dyes stain protein by only non-covalent interactions with the protein (i.e., by forming only non-covalent complexes with the protein).

It has been discovered, surprisingly, that the interaction of an enhanced hydrophobicity dye with protein is advantageously altered, in comparison with the interaction with protein of the corresponding, unmodified, dye. These advantageous changes are evident in uses of the dyes in protein detection, analysis and quantitation, including such uses involving electrophoretic separation of proteins in inert supports, such as polyacrylamide or agarose gels, including such gels which have protein-denaturing detergents such as sodium dodecyl sulfate.

The enhanced hydrophobicity dyes employed in the novel methods of the invention, including the novel dyes of the invention, are, like the prior art dyes from which they can be made, preferably from one of the classes of dyes known as triphenylmethane dyes (and, more specifically, rosaniline dyes), acid blue 25 dyes, dansyl dyes, fluorescein dyes, or 2-methoxy-2,4-diphenyl-3(2H)-furanone ("MDPF") dyes. Preferably, the triphenylmethane dyes of the invention are modified (i.e., derivatized) Coomassie dyes.

Some of the enhanced hydrophobicity dyes, which are employed in or are part of the invention, such as Coomassie dyes and Acid Blue 25 dyes, visibly stain protein, i.e., form dye-protein complexes which are colored and, as such, can be detected visually (with the unassisted human eye) or spectrophotometrically (using a spectrophotometric device).

Some of the enhanced hydrophobicity dyes, employed in or part of the invention, such as dansyl dyes, fluorescein dyes, and MDPF dyes, are fluorescent. While many of these fluorescent dyes are also colored, they can be detected more sensitively through their fluorescence, e.g., such as by using a "transilluminator," as understood in the art.

The novel, modified dyes of the invention, and the other enhanced hydrophobicity dyes employed in the methods of the invention, have a number of unexpected advantages over the corresponding, polar-functional-group-containing dyes in staining proteins and, on account of their increased hydrophobicity, provide a number of novel and improved methods for detecting, analyzing and quantitating proteins, especially proteins in solution or separated or fractionated from a sample of proteins with a process such as electrophoresis. Thus, for example, the enhanced hydrophobicity dyes allow proteins during electrophoresis to be detected, by visualization or by observation of fluorescence, with significantly improved sensitivity because the dyes have improved affinity for proteins in competition with the support, which may be left essentially colorless, showing bands of stained protein on an essentially clear background.

In addition, the modified rosanaline dyes of the invention have a number of additional unexpected advantages over unmodified Coomassie dyes which permit the sensitive detection and quantitation of proteins by rapid color-enhancement and destaining methods that, in turn, for example, can be used to quickly prepare a sample of protein for other methods of protein analysis (e.g., sequence analysis) or quantification; and permit sensitive quantitation of proteins in solution at pH's between about 3.5 and about 8.5, significantly milder that the very low pH's required for such purposes with unmodified Coomassie dyes.

The invention encompasses a dye of Formula I

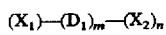

wherein $D_1$ is selected from the group consisting of (i) a moiety of Formula X

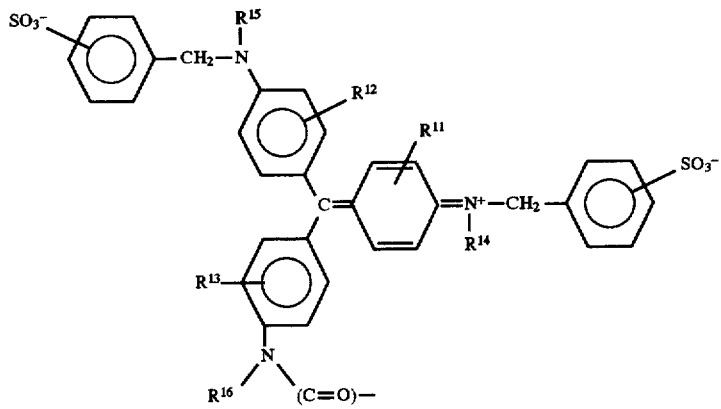

wherein $R^{11}$, $R^{12}$ and $R^{13}$ are independently selected from the group consisting of hydrogen and alkyl of 1–6 carbon atoms; $R^{14}$ and $R^{15}$ are independently selected from the group consisting of alkyl of 1–6 carbon atoms; and $R^{16}$ is selected from the group consisting of alkyl of 1–20 carbon atoms, phenyl, alkoxyphenyl, wherein the alkyl group is of 1–10 carbon atoms, and alkylphenyl, wherein the alkyl group is of 1–10 carbon atoms;

(ii) a moiety of Formula XX

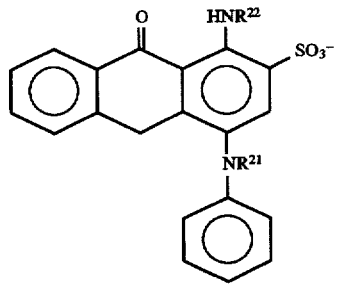

wherein $R^{21}$ and $R^{22}$ are independently selected from the group consisting of hydrogen and —(C=O)—, provided that at least one of $R^{21}$ and $R^{22}$ is —(C=O)—;

(iii) a fluorescein moiety of Formula XXXA

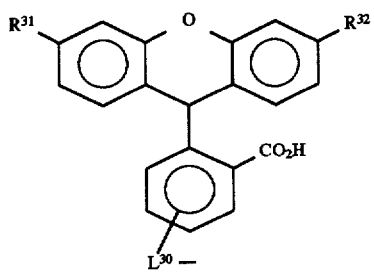

wherein the —$L^{30}$— moiety is selected from the group consisting of —(NH)(C=S)NH—; —$SO_2$NH—, wherein the sulfur of the sulfonyl group is bonded directly to the phenyl bearing the —$CO_2$H moiety; —(C=O)NH—, wherein the carbon of the —(C=O)— group is bonded directly to the phenyl bearing the —$CO_2$H moiety; —$CH_2$S—, wherein the carbon of the —$CH_2$— group is bonded directly to the phenyl bearing the —$CO_2$H moiety; —S—; and —NH(C=O)$CH_2$S—, wherein the nitrogen of the —(NH) is bonded directly to the phenyl bearing the —$CO_2$H moiety; and is para or meta to the —$CO_2$H moiety; wherein $R^{31}$ is selected from the group consisting of —OH and

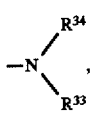

wherein $R^{33}$ and $R^{34}$ are independently selected from alkyl of 1–6 carbon atoms, $R^{32}$ is oxygen if $R^{31}$ is —OH and is

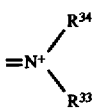

if $R^{32}$ is

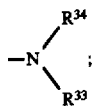

(iv) a moiety of Formula XL

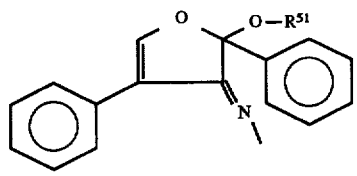

wherein $R^{51}$ is selected from the group consisting of hydrogen and alkyl of 1–6 carbon atoms; and (v) a moiety of Formula LXX

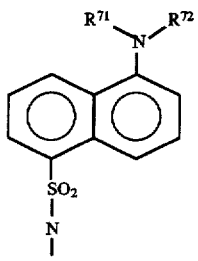

LXX wherein $R^{71}$ and $R^{72}$ are independently selected from alkyl of 1–10 carbon atoms;

wherein m is the number of moieties $D_1$ in each molecule of dye and is 1 or 2 and n is the number of moieties $X_2$ in each molecule of dye and is 0 or 1;

wherein, if $D_1$ is of Formula X, m is 1 and n is 0 and $X_1$ is selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano;

wherein, if $D_1$ is of Formula XX, m is 1 and n is 0, if either of $R^{21}$ and $R^{22}$ is H, or 1, and $X_1$ and $X_2$ are independently selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano;

wherein, if $D_1$ is of Formula XXXA, m is 1 or 2 and n is 0, and $X_1$ is selected from the group consisting of:

(i) —$X_3$—$R^{62}$, wherein —$X_3$— is alkylenyl of 1–20 carbon atoms and $R^{62}$ is at any one position in $X_3$ and is hydrogen, bromo, chloro, hydroxyl,

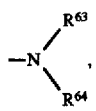

—(C=O)O$R^{63}$, or, if m is 2, a single bond to the second moiety of formula XXXA, wherein $R^{63}$ and $R^{64}$ are independently selected from hydrogen and alkyl of 1–10 carbon atoms;

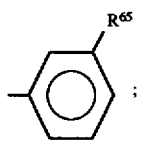     (ii)

and

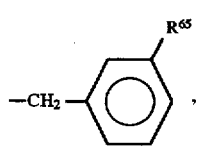    (iii)

wherein $R^{65}$ is bromo, chloro, cyano, nitro,

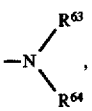

—(C=O)O$R^{63}$, or, if m is 2, a single bond to the second moiety of formula XXXA;

wherein, if $D_1$ is of Formula LXX, m is 1 or 2 and n is 0, and $X_1$ is selected from the group consisting of:

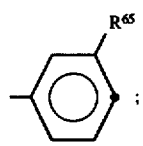    (i)

and

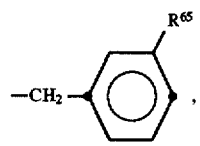    (ii)

wherein $R^{65}$ is bromo, chloro, cyano, nitro,

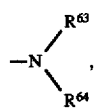

—(C=O)O$R^{63}$, or, if m is 2, a single bond to the second moiety of formula LXX; and wherein, if $D_1$ is of Formula XL, m is 1 or 2 and n is 0, and $X_1$ is selected from the group consisting of:

(i) —$X_3$—$R^{66}$, wherein $R^{66}$ is at any one position in $X_3$ and is hydrogen, bromo, chloro, hydroxyl,

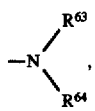

—(C=O)O$R^{63}$ or, if m is 2, a single bond to the second moiety of formula XL;

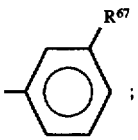    (i)

and

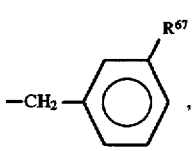    (ii)

wherein R[67] is bromo, chloro, cyano, nitro,

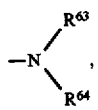

—(C=O)OR[63], or, if m is 2, a single bond to the second moiety of formula XL;
or a salt of a dye of Formula I.

The invention further encompasses a method of detecting a protein which comprises (A) making a complex of the protein with a dye of Formula II

wherein $D_1$ is selected from the group consisting of (i) a moiety of Formula X

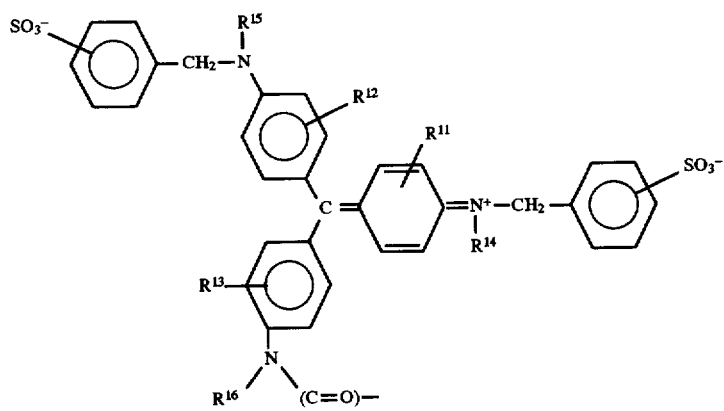

wherein $R^{11}$, $R^{12}$ and $R^{13}$ are independently selected from the group consisting of hydrogen and alkyl of 1–6 carbon atoms;

$R^{14}$ and $R^{15}$ are independently selected from the group consisting of alkyl of 1–6 carbon atoms; and $R^{16}$ is selected from the group consisting of alkyl of 1–20 carbon atoms, phenyl, alkoxyphenyl, wherein the alkyl group is of 1–10 carbon atoms, and alkylphenyl, wherein the alkyl group is of 1–10 carbon atoms;

(ii) a moiety of Formula XX

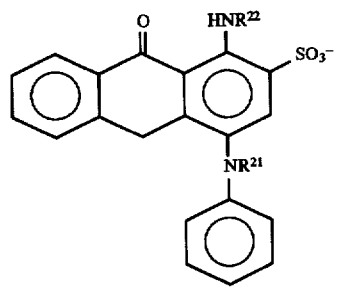

wherein $R^{21}$ and $R^{22}$ are independently selected from the group consisting of hydrogen and —(C=O)—, provided that at least one of $R^{21}$ and $R^{22}$ is —(C=O)—;

(iii) a fluorescein moiety of Formula XXXA

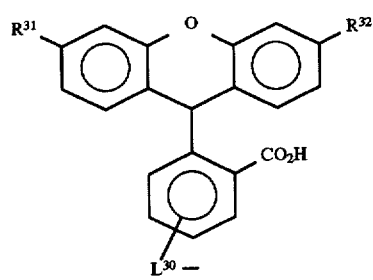

wherein the —$L^{30}$— moiety is selected from the group consisting of —(NH)(C=S)NH—; —SO$_2$NH—, wherein the sulfur of the sulfonyl group is bonded directly to the phenyl bearing the —CO$_2$H moiety; —(C=O)NH—, wherein the carbon of the —(C=O)— group is bonded directly to the phenyl bearing the —CO$_2$H moiety; —CH$_2$S—, wherein the carbon of the —CH$_2$— group is bonded directly to the phenyl bearing the —CO$_2$H moiety; —S—; and —NH(C=O)CH$_2$S—, wherein the nitrogen of the —(NH) is bonded directly to the phenyl bearing the —CO$_2$H moiety; and is para or meta to the —CO$_2$H moiety; wherein $R^{31}$ is selected from the group consisting of —OH and

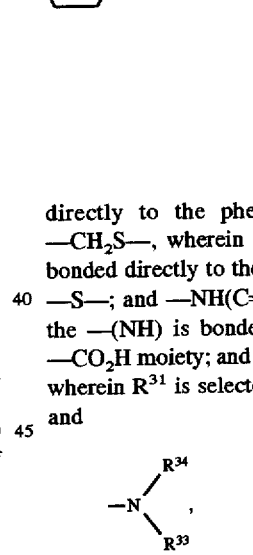

wherein $R^{33}$ and $R^{34}$ are independently selected from alkyl of 1–6 carbon atoms, $R^{32}$ is oxygen if $R^{31}$ is —OH and is

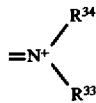

if $R^{32}$ is

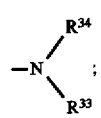

(iv) a moiety of Formula XL

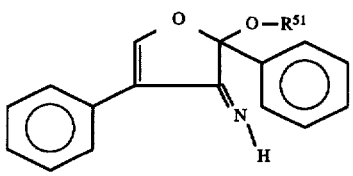

wherein $R^{51}$ is selected from the group consisting of hydrogen and alkyl of 1–6 carbon atoms; and (v) a moiety of Formula LXX

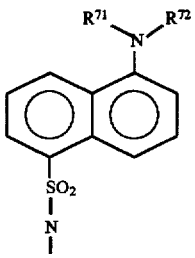

wherein $R^{71}$ and $R^{72}$ are independently selected from alkyl of 1–10 carbon atoms;

wherein m is the number of moieties $D_1$ in each molecule of dye and is 1 or 2 and n is the number of moieties $X_2$ in each molecule of dye and is 0 or 1;

wherein, if $D_1$ is of Formula X, m is 1 and n is 0 and $X_{11}$ is selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano;

wherein, if $D_1$ is of Formula XX, m is 1 and n is 0, if either of $R^{21}$ and $R^{22}$ is H, or 1, and $X_{11}$ and $X_2$ are independently selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano;

wherein, if $D_1$ is of Formula XXXA or Formula LXX, m is 1 or 2 and n is 0, and X11 is selected from the group consisting of:

(i) —$X_3$—$R^{62}$, wherein —$X_3$— is alkylenyl of 1–20 carbon atoms and $R^{62}$ is at any one position in $X_3$ and is hydrogen, bromo, chloro, hydroxyl,

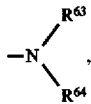

—(C=O)$OR^{63}$, or, if m is 2, a single bond to the second moiety of Formula XXXA, if $D_1$ is of Formula XXXA, or the second moiety of Formula LXX, if $D_1$ is of formula LXX, and wherein $R^{63}$ and $R^{64}$ are independently selected from hydrogen and alkyl of 1–10 carbon atoms;

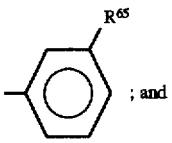
(ii)
; and

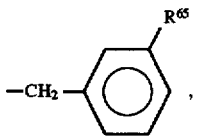
(iii)

wherein $R^{65}$ is bromo, chloro, R cyano, nitro,

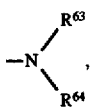

—(C=O)$OR^{63}$, or, if m is 2, a single bond to the second moiety of Formula XXXA, if $D_1$ is of Formula XXXA, or the second moiety of Formula LXX, if $D_1$ is of formula LXX; and wherein, if $D_1$ is of Formula XL, m is 1 or 2 and n is 0, and $X_{11}$ is selected from the group consisting of:

(i) —$X_3$—$R^{66}$, wherein $R^{66}$ is at any one position in $X_3$ and is hydrogen, bromo, chloro, hydroxyl,

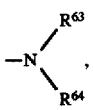

—(C=O)$OR^{63}$ or, if m is 2, a single bond to the second moiety of Formula XL;

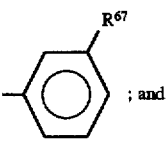
(ii)
; and

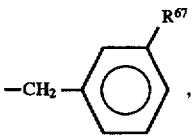
(iii)

wherein $R^{67}$ is bromo chloro cyano, nitro,

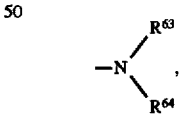

—(C=O)$OR^{63}$ or, if m is 2, a single bond to the second moiety of Formula XL;

and (B) detecting the complex by (i) if $D_1$ in the dye is of Formula X or XX, observing the color of the complex due to the presence of the dye of Formula II in the complex or (ii) if $D_1$ in the dye is of Formula XXXA, XL or LXX, observing the color or the fluorescence of the complex due to the presence of the dye of Formula II in the complex.

Still further, the invention encompasses a method of detecting protein in a sample comprising the steps of:

(a) applying a sample solution comprising a protein to a polyacrylamide or agarose gel;

(b) separating the sample into protein fractions using electrophoresis;

(c) staining the protein on the support with a dye of Formula II $$(X_{11})-(D_1)_m-(X_2)_n \qquad II$$

wherein $D_1$ is selected from the group consisting of (i) a moiety of Formula X

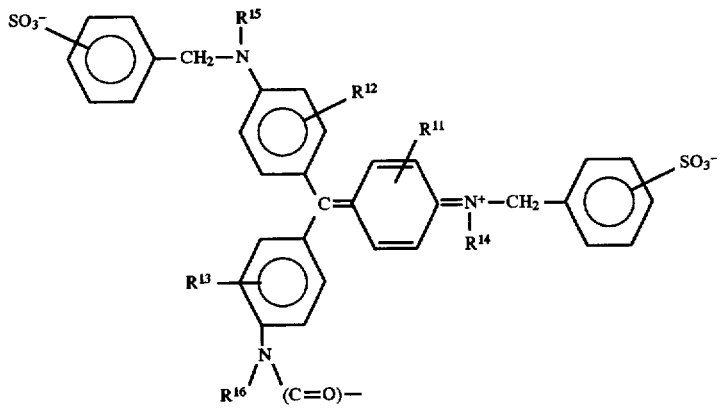

wherein $R^{11}$, $R^{12}$ and $R^{13}$ are independently selected from the group consisting of hydrogen and alkyl of 1–6 carbon atom; $R^{14}$ and $R^{15}$ are independently selected from the group consisting of alkyl of 1–6 carbon atoms; and $R^{16}$ is selected from the group consisting of alkyl of 1–20 carbon atoms, phenyl, alkoxyphenyl, wherein the alkyl group is of 1–10 carbon atoms, and alkylphenyl, wherein the alkyl group is of 1–10 carbon atoms;

(ii) a moiety of Formula XX

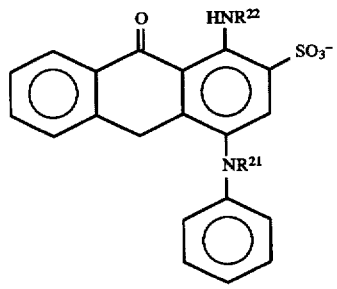

wherein $R^{21}$ and $R^{22}$ are independently selected from the group consisting of hydrogen and —(C=O)—, provided that at least one of $R^{21}$ and $R^{22}$ is —(C=O)—;

(iii) a fluorescein moiety of Formula XXXA

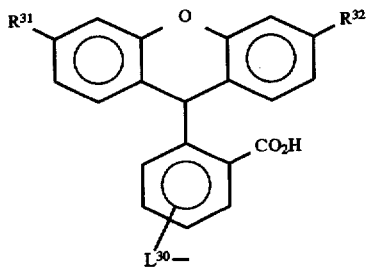

wherein the —$L^{30}$— moiety is selected from the group consisting of —(NH)(C=S)NH—; —$SO_2$NH—, wherein the sulfur of the sulfonyl group is bonded directly to the phenyl bearing the —$CO_2H$ moiety; —(C=O)NH—, wherein the carbon of the —(C=O)— group is bonded directly to the phenyl bearing the —$CO_2H$ moiety; —$CH_2S$—, wherein the carbon of the —$CH_2$— group is bonded directly to the phenyl bearing the —$CO_2H$ moiety; —S—; and —NH(C=O)$CH_2S$—, wherein the nitrogen of the —(NH) is bonded directly to the phenyl bearing the —$CO_2H$ moiety; and is pard or meta to the —$CO_2H$ moiety; wherein $R^{31}$ is selected from the group consisting of —OH and

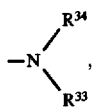

wherein $R^{33}$ and $R^{34}$ are independently selected from alkyl of 1–6 carbon atoms, $R^{32}$ is oxygen if $R^{31}$ is —OH and is

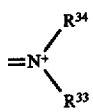

if $R^{32}$ is

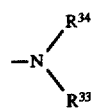

(iv) a moiety of Formula XL

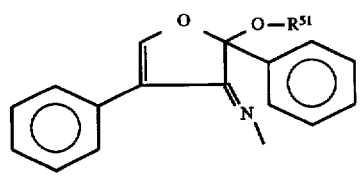

wherein $R^{51}$ is selected from the group consisting of hydrogen and alkyl of 1–6 carbon atoms; and (v) a moiety of Formula LXX

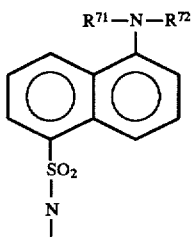
LXX wherein $R^{71}$ and $R^{72}$ are independently selected from alkyl of 1–10 carbon atoms;

wherein m is the number of moieties $D_1$ in each molecule of dye and is 1 or 2 and n is the number of moieties $X_2$ in each molecule of dye and is 0 or 1;

wherein, if $D_1$ is of Formula X, m is 1 and n is 0 and $X_{11}$ is selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano;

wherein, if $D_1$ is of Formula XX, m is 1 and n is 0, if either of $R^{21}$ and $R^{22}$ is H, or 1, and $X_{11}$ and $X_2$ are independently selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano; wherein, if $D_1$ is of Formula XXXA or Formula LXX, m is 1 or 2 and n is 0, and $X_{11}$ is selected from the group consisting of:

(i) —$X_3$—$R^{62}$, wherein —$X_3$— is alkylenyl of 1–20 carbon atoms and $R^{62}$ is at any one position in $X_3$ and is hydrogen, bromo, chloro, hydroxyl,

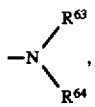,

—(C=O)O$R^{63}$, or, if m is 2, a single bond to the second moiety of Formula XXXA, if $D_1$ is of Formula XXXA, or the second moiety of Formula LXX, if $D_1$ is of formula LXX, and wherein $R^{63}$ and $R^{64}$ are independently selected from hydrogen and alkyl of 1–10 carbon atoms;

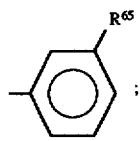 (ii)

and

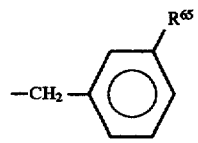 (iii)

wherein $R^{65}$ is bromo, chloro, cyano, nitro,

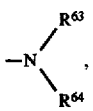,

—(C=O)O$R^{63}$, or, if m is 2, a single bond to the second moiety of Formula XXXA, if $D_1$ is of Formula XXXA, or the second moiety of Formula LXX, if $D_1$ is of formula LXX; and wherein, if $D_1$ is of Formula XL, m is 1 or 2 and n is 0, and $X_{11}$ is selected from the group consisting of:

(i) —$X_3$—$R^{66}$, wherein $R^{66}$ is at any one position in $X_3$ and is hydrogen, bromo, chloro, hydroxyl,

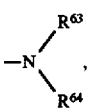,

—(C=O)O$R^{63}$ or, if m is 2, a single bond to the second moiety of Formula XL;

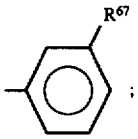 (ii)

and

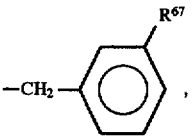 (iii)

wherein $R^{67}$ is bromo, chloro, cyano, nitro,

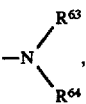,

—(C=O)O$R^{63}$ or, if m is 2, a single bond to the second moiety of Formula XL: and (d) detecting the stained protein by (i) if $D_1$ in the dye is of Formula X or XX, observing the color of the complex due to the presence of the dye of Formula II in the complex or (ii) if $D_1$ in the dye is of Formula XXXA, XL or LXX, observing the color or the fluorescence of the complex due to the presence of the dye of Formula II in the complex.

The invention still further encompasses a method of detecting a protein in a polyacrylamide or agarose support, in which the protein has been electrophoresed, comprising:

(A) staining the protein in the support with a dye of Formula III $(S_{12})$—$(D_3)$    III wherein $D_3$ is a moiety of Formula X

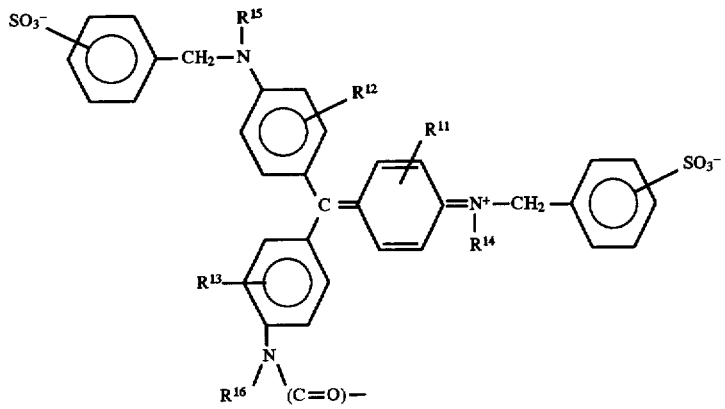

X wherein $R^{11}$, $R^{12}$ and $R^{13}$ are independently selected from the group consisting of hydrogen and alkyl of 1–6 carbon atoms; $R^{14}$ and $R^{15}$ are independently selected from the group consisting of alkyl of 1–6 carbon atoms; and $R^{16}$ is selected from the group consisting of alkyl of 1–20 carbon atoms, phenyl, alkoxyphenyl, wherein the alkyl group is of 1–10 carbon atoms, and alkylphenyl, wherein the alkyl group is of 1–10 carbon atoms; and wherein $X_{12}$ is selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano; and (B) bathing the support in an aqueous solution with a pH less than about 3, and (C) visualizing the stained protein.

Dyes of Formula II are exemplary of enhanced hydrophobicity dyes. Enhanced hydrophobicity dyes of Formula I are exemplary of novel dyes of the invention.

Dyes in which $D_1$ is of Formula X are Coomassie dyes. Dyes in which $D_1$ is of Formula XX are Acid Blue 25 dyes. Dyes in which $D_1$ is of Formula XXXA are fluorescein dyes. Dyes in which $D_1$ is of Formula XL are MDPF dyes. Dyes in which $D_1$ is of Formula LXX are dansyl dyes.

In the more preferred Coomassie dyes of the invention, $R^{11}$, $R^{12}$, and $R^{13}$ are independently selected from the group consisting of hydrogen and alkyl of 1–6 carbon atoms; $R^{14}$ and $R^{15}$ are independently selected from the group consisting of alkyl of 1–6 carbon atoms; $R^{16}$ is selected from the group consisting of alkyl of 1–20 carbon atoms, phenyl, alkoxyphenyl, wherein the alkyl group is of 1–10 carbon atoms, and alkylphenyl, wherein the alkyl group is of 1–10 carbon atoms; and $X^1$ is selected from the group consisting of alkyl of 1–20 carbon atoms, phenyl, benzyl, phenyl substituted at any one position with alkyl of 1–10 carbon atoms, chloro, bromo, nitro, or cyano, and benzyl substituted at any one position on the phenyl ring with alkyl of 1–10 carbon atoms, chloro, bromo, nitro or cyano.

In still more preferred Coomassie dyes of the invention, $R^{11}$ and $R^{12}$ are both hydrogen or both methyl; $R^{13}$ is hydrogen; $R^{14}$ and $R^{15}$ are both ethyl; $R^{16}$ is ethyl or ethoxyphenyl; and $X_1$ is selected from the group consisting of alkyl of 1–20 carbon atoms and phenyl. Still more preferred are the dyes wherein $R^{11}$ and $R^{12}$ are both hydrogen or both methyl; $R^{13}$ is hydrogen; $R^{14}$ and $R^{15}$ are both ethyl; $R^6$ is ethoxyphenyl; and $X_1$ is selected from the group consisting of alkyl of 2–10 carbon atoms and phenyl.

The Coomassie dye wherein $R^{11}$, $R^{12}$ and $R^{13}$ are all hydrogen; $R^{14}$ and $R^{15}$ are both ethyl; $R^{16}$ is ethoxyphenyl; and $X_1$ is n-heptyl is called "Promega Green 1." The Coomassie dye wherein $R^{11}$, $R^{12}$ and $R^{13}$ are all hydrogen; $R^{14}$ and $R^{15}$ are both ethyl; $R^{16}$ is ethoxyphenyl; and $X_1$ is methyl is called "Promega Green 2." The Coomassie dye wherein $R^{11}$, $R^{12}$ and $R^{13}$ are all hydrogen; $R^{14}$ and $R^{15}$ are both ethyl; $R^{16}$ is ethoxyphenyl; and $X_1$ is n-undecyl is called "Promega Green 3."

Reference herein to an "alkyl" group, without further qualification except as to number of carbons, is to a straight-chain, branched-chain, or cyclic alkyl group, that may be substituted with alkyl groups.

Preferred among the Acid Blue 25 dyes of the invention and for use in the methods of the invention are those wherein, with reference to Formula II, n is 0 or 1 and $X_{11}$ and $X_2$ are independently selected from n-alkyl of 1–12 carbon atoms. In the more preferred Acid Blue 25 dye, n is 1 and $X_{11}$ and $X_2$ are heptyl.

Preferred among the fluorescein dyes of the invention are those which are fluorescein thiourea or fluorescein isothiocyanate derivatives, wherein, with reference to Formula II, $D_1$ is a moiety of Formula XXX

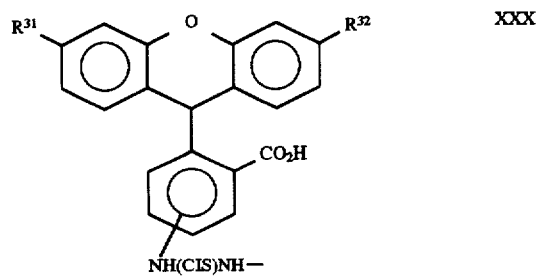

XXX wherein, with reference to Formula XXX, the —(NH)(C=S)NH— moiety is meta to the —$CO_2H$ moiety. In the more preferred fluorescein thiourea dyes, $R^{31}$ is —OH and $X_{11}$ is selected from the group consisting of alkyl of 1–20 carbon atoms and

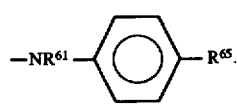

Still more preferred among the fluorescein thiourea dyes are those wherein, in the dye, $X_1$ is selected from the group consisting of n-alkyl of 1–12 carbons, a single bond joining two moieties of Formula XXX, —(C=O)$OR^{68}$, wherein $R^{68}$ is hydrogen or alkyl of 1–3 carbons,

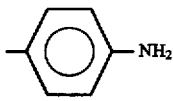

and, joining two moieties of Formula XXX,

Yet still more preferred among the fluorescein thiourea dyes are those wherein $X_1$ is selected from the group consisting of n-octyl, n-dodecyl,

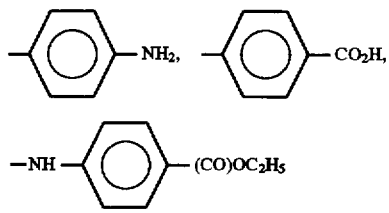

and, joining two moieties of Formula XXX,

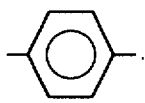

Preferred among the MDPF dyes of the invention are those wherein, with reference to Formula II —$X_3$—$R^{66}$ is selected from the group consisting of alkyl of 1–20 carbon atoms, phenyl and benzyl. More preferred among the MDPF dyes are those wherein, in the dye, $R^{51}$ is ethyl and —$X_3$—$R^{66}$ is n-alkyl of 1–12 carbon atoms.

Preferred among the dansyl dyes for use in the methods of the invention, and of the invention, are those wherein, with reference to Formula II, $R^{71}$ and $R^{72}$ are both methyl, and $X_{11}$ is selected from the group consisting of alkyl of 1–20 carbon atoms and

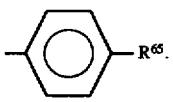

More preferred among the dansyl dyes are those wherein $X_{11}$ is selected from the group consisting of alkyl of 1–12 carbons, —(C=O)O$R^{68}$, wherein $R^{68}$ is hydrogen or alkyl of 1–3 carbons,

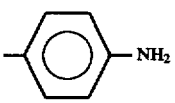

and, joining two moieties,

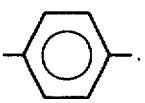

Still more preferably, for the dansyl dyes, $X_{11}$ is selected from the group consisting of n-alkyl of 1–12 carbon atoms,

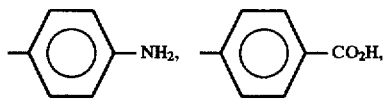

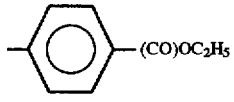

and, joining two moieties,

Most preferably, in the dansyl dyes, $X_{11}$ is selected from the group consisting of n-alkyl of 8–12 carbon atoms.

A Coomassie dye of Formula I (or Formula II or III) is readily synthesized by the skilled beginning with, as starting material, the corresponding compound, which has the same substituents, $R^{11}$, $R^{12}$, $R^{13}$, $R^{14}$, $R^{15}$ and $R^{16}$, as the Coomassie dye that is to be made but has, in place of substituent —(C=O)$X_1$ (or —(C=O)$X_{11}$ or —(C=O)$X_{12}$) in said dye, hydrogen. These starting materials, which are, or are simple derivatives of, triphenylmethane dyes, for which methods of synthesis are well known, are readily prepared by the skilled; indeed many of them, such as Coomassie Blue R and Coomassie Blue G, are commercially available.

To prepare a Coomassie dye of Formula I (or II or III), the corresponding compound is treated with the corresponding acylating agent, such as the corresponding cylchloride or anhydride, using methods well known to the skilled organic chemist. A preferred solvent for the acylation reaction is pyridine, and the reaction proceeds well in that solvent refluxing at atmospheric pressure.

An acid blue 25 dye of Formula I (or Formula II) is readily synthesized by the skilled similarly to a Coomassie dye of Formula I beginning with, as starting material, the corresponding acid blue 25 compound, which has the same substituents, other than $X_1$ and $X_2$, as the desired compound. The corresponding acid blue 25 compound is known (e.g., acid blue 25 itself), or readily prepared by the skilled using standard techniques. To obtain the desired acid blue 25 dye of the invention, the corresponding acid blue 25 compound is acylated, by a method closely similar to that employed with Coomassie dyes, with the corresponding acylating agent(s). If $X_1$ is different from $X_2$, two acylating agents, one to provide $X_1$ and the other to provide $X_2$, are used.

After the acylation reaction to prepare a Coomassie or acid blue 25 derivative, steps are taken to destroy excess acylating reagent (by, e.g., addition of methanol or water) and remove most of the solvent (e.g., by rotary evaporation). The residue after the evaporation can be taken up in a suitable solvent, such as methanol or aqueous methanol with more than about 25 % (v/v) methanol, and the resulting solution used in protein staining, typically after further dilution in an alcohol or aqueous solution (including a buffer solution used in electrophoresis), as illustrated in the following examples. Alternatively, after elimination of excess acylating reagent and removal of solvent (in the case of pyridine, by rotary evaporation followed by azeotropic distillation once or twice with toluene), the derivative can be isolated by a standard technique (e.g., thin-layer chromatography on silica gel, silica gel column chromatography). The isolated derivative can then be taken up in a suitable solvent (e.g., 1:1 methanol:water) and the resulting solution used in protein staining, typically after further dilution in an alcohol or aqueous solution (including a buffer solution used in electrophoresis), as illustrated in the examples.

A fluorescein thiourea dye of Formula I (or Formula II), an MDPF dye of Formula I (or Formula II), or a dansyl dye of Formula I (or Formula II) are readily synthesized from the corresponding fluorescein isothiocyanate (i.e., compound with Formula XXX except that the —NH(C=S)NH— moiety is replaced with an isothiocyanato moiety), MDPF (i.e., compound with Formula XL except that the =N— is replaced with =O), or dansyl halide (i.e., compound with Formula LXX except that the —($SO_2$)NH— is replaced with a sulfonyl chloride or sulfonyl bromide), respectively, and an amine of formula ($HNR^{61}$)$X_3R^{62}$, wherein $R^{61}$ is hydrogen or alkyl of 1–10 carbons (preferably hydrogen) in the case of a fluorescein thiourea or dansyl dye, or formula ($NH_2$)$X_3R^{66}$, in the case of an MDPF dye. The reaction can be carried out conveniently at room temperature under basic conditions in a polar organic solvent or a mixture of such solvents (e.g., acetone, dimethylformamide (i.e., N,N-dimethylformamide)) or a mixture of water and such a solvent(s). Illustrative reaction conditions are provided in the following examples. The desired fluorescein thiourea derivative, MDPF derivative or dansyl derivative can then be isolated, if desired, using standard methodology (e.g., silica gel column chromatography, thin-layer chromotagrpahy). The isolated derivative can then be taken up in a suitable solvent, typically ethanol, methanol, or aqueous solutions thereof, for use in staining, as described in greater detail in the examples that follow. Alternatively, and again with reference to the examples below, the reaction mixtures, in which the derivatives were synthesized, can simply be diluted from about 10-fold to about 1000-fold with such a solvent (e.g., 10 % aqueous methanol) and used in protein staining without need for purification of the derivative from the reaction mixture in which the derivative was made.

As described hereinabove and as the skilled will readily understand, the present invention also encompasses salts of the novel dyes of the invention and the use of salts of enhanced hydrophobicity dyes in the methods of the invention. By "salt" is intended a compound which combines a neutral (i.e., zero-charged) compound of the invention (even if it includes charged groups which, when considered together, have a net charge of 0) with another neutral, salt-forming compound, typically an acid (e.g., HCl) or base (e.g., NaOH), as understood in the art. For example, salts of Coomassie dyes which do not include an amino group in $X_1$, fluorescein thiourea dyes (wherein $R^{31}$ is —OH) which do not include an amino group in $X_1$, and Acid Blue 25 dyes in which both nitrogens are acylated and which do not include an amino group in $X_1$ or $X_2$, include the salts with sodium, potassium, magnesium, calcium, ammonium, mono, di-, tri- or tetra-alkyl-substituted ammonium or the like. Sodium is preferred. For example, further, salts of dansyl dyes, fluorescein thiourea dyes (wherein $R_{31}$ is dialkyl amino), acid blue 25 dyes in which both nitrogens are acylated and which include two amino groups, and MDPF dyes in which $X_1$ includes an amino group include acid addition salts with HCl, HBr, sulfuric acid, methylsulfonic acid, nitric acid, phosphoric acid, acetic acid, citric acid, lactic acid, or the like. HCl is preferred. The salts are preferably "electrophoretically acceptable salts," by which is meant that the ion of the salt (other than the charged dye molecule) will interact with the dye only non-covalently and will migrate in an electric field through an electrophoretic solid support used to separate proteins much more rapidly than protein. Preparation of salts of the dyes of the invention is straightforward for the skilled chemist, entailing simply combining a solution of the neutral dye with a base, acid or a salt, in which the cation or anion is the cation or anion, respectively, intended for the salt with the dye. The resulting solution of the salt may then be used in protein staining similarly to solutions of the neutral dye, optionally after further dilution with an alcoholic or aqueous solution (including possibly a standard buffer solution used for protein electrophoresis). Alternatively, the solution resulting from combining a solution of the neutral dye with an acid, base or salt can be placed under conditions which cause precipitation from the solution of the desired salt of the dye. Then, if desired, further steps, well known to the skilled, to isolate and purify the precipitated salt can be taken. For use in protein staining, a precipitated salt is treated in essentially the same way as the corresponding neutral derivative, if obtained in solid form, would be treated, by being taken up in a suitable alcoholic or aqueous solution, which in turn, before actual use in staining, may be further diluted with an alcoholic or aqueous solution (including a buffer solution for protein electrophoresis).

Although the various dyes are represented herein with particular structural formulas, each of which indicates only one protonated or unprotonated state for each acid or base group, the skilled will understand that, in a real aqueous system, the various forms of a dye are in a dynamic equilibrium with one another and other components of the system and that a group on a particular dye molecule might be protonated differently from what is indicated in a structural formula for the dye. The structural formula for a dye is intended to represent the dye as a whole and not any particular molecule thereof.

The $X_1$, $X_2$, $X_{11}$ and $X_{12}$ groups (hereinafter referred to collectively as "the X groups") increase the hydrophobicity of an enhanced hydrophobicity dye in comparison with the corresponding underivatized dye. As will become apparent from the description below, the X groups function to enhance (relative to the corresponding, underivatized compound) the ability of the dye of the invention to stain protein preferentially to staining a gel or solid support comprising the protein. Presumably the X groups enhance (relative to the corresponding underivatized compound) the affinity of an enhanced hydrophobicity dye for protein while at the same time not affecting or perhaps even decreasing (again, relative to the corresponding, underivatized compound) the affinity of the dye for the gel or solid support.

The method of the invention involves the use of the above-described enhanced hydrophobicity dyes to detect proteins wherein the complex of the dye with the protein is colored or fluorescent (or both) and, consequently, renders the protein detectable by visualization or spectrophotometrically or with the aid of a device to detect fluorescence. More specifically, the invention involves the use of the above-described dyes for detecting protein in solution or using routine electrophoretic techniques well known to artisans in the field of the invention. Hames, B. and Rickwood, D., supra.

The term "protein" is meant to include any protein-like substance, including polypeptides, peptides, radioactive and non-radioactive labeled proteins, glycoproteins, lipoproteins, protein components or subunits, fragments resulting from partial proteolysis of a protein or mixtures thereof, or the like, to which at least one molecule of an enhance hydrophobicity dye in accordance with the invention is capable of complexing. In electrophoretic applications, the "protein" will typically and preferably have a molecular weight of at least about 1000 daltons.

According to the broad invention, proteins in a sample, which could be a sample of a fluid, such as blood or blood serum, lymph, ascites fluid, urine, microorganism or tissue culture medium, cell extract, or the like derived from a biological source, or a solution thought to include chemically synthesized protein, or an extract or solution prepared from such a fluid from a biological source or solution thought to contain synthesized protein, is applied to a solid support. Preferably, the solid support is a gel, most preferably made either of polyacrylamide or agarose. The protein sample on the solid support is then separated into protein fractions using electrophoresis; the solid support may be prepared to include the enhance hydrophobicity dye prior to the electrophoresis or the support with the protein fractions may be stained after the electrophoresis with such a dye; in either case, the solid support may be destained so that only the protein fractions retain substantial color or fluorescence (or both) due to the dye; and, the stained proteins are detected qualitatively and/or quantitatively, on the basis of the color or fluorescence imparted to them by the dye with which they are complexed. Qualitative detection may involve visualization of the solid support directly or, in the case of fluorescent dyes, a transilluminator or of a photograph of the solid support (in the case of a fluorescent dye, made with the aid of a transilluminator); quantitation may be accomplished using spectrophotometry, densitometry, fluorescence intensity measurements, or any other technique known to artisans in the field of protein electrophoresis. The preferred electrophoresis method of the invention uses sodium dodecyl sulfate in a polyacrylamide support (SDS-PAGE). Such method is commonly known to those skilled in the field of the invention. Hames, B. and Rickwood, D. supra and Wilson, C. supra. However, the present invention may also be practiced using native-gels, including polyacrylamide gels, wherein intrinsic properties of the proteins, such as three-dimensional structure and enzymatic activity, are retained.

An aspect of the method of the present invention is that the protein fractions advantageously may be visualized during the electrophoresis process, as described in, for example, Examples 5, 7, 9, 22 and 24, below. This feature of the invention is attributable to the fact that the gel remains essentially colorless while the dye of the invention stains the separating protein fractions.

Another aspect of the method of the invention relates to the advantageous rapidity with which proteins may be detected. For instance, smaller amounts of protein than can be visualized as the gel is running (as described in Examples 5, 7 and 9) can be visualized in only 1-2 minutes, as described in Examples 6, 8 and 10. Still smaller amounts of protein can be visualized employing the only slightly longer protocol described in Example 12.

A further aspect of the method of the invention relates to the advantageously high sensitivity with which the dyes of the invention permit protein to be detected. For instance, the protocols described in Examples 14 and 15 permit the highly sensitive quantitation of protein in solution and SDS-PAGE, respectively.

Another aspect of the method of the invention relates to sensitive post-electrophoretic staining of proteins within gel matrices. For instance, small amounts of proteins can be observed fluorescently as described in Examples 27, 30, 31, 34, 37 and 39.

In another aspect, the invention provides for more rapid detection, via fluorescence, of protein in gel matrices by the application of in-gel staining of the protein species, as described, for example, in Examples 32 and 35. By use of an apparatus whereby the electrophoresis gel were positioned such as to allow light, capable of exciting the fluorescence of the fluorescent dyes of the invention, to penetrate to the locations of the electrophoretically fractionating protein species, the proteins in the samples should be observable as fluorescent bands during the electrophoretic separation. This is already possible with visible dyes of the invention, as indicated, for example, in Examples 5, 7, 9, 22 and 24.

Although the enhanced hydrophobicity dyes of the invention do not discriminate among protein species, in the extent of their binding thereto, to the same extent as dyes which interact covalently with proteins, some of the dyes of the invention, particularly those which include charged groups, do display different extents of binding to different proteins which allows the dye to be used to detect some proteins much more sensitively than others. This is seen, for example, in Example 37. This differential binding capability (and associated differences in sensitivity with which different proteins can be detected) permits, under certain circumstances, detection of specific protein(s) in a mixture of proteins. This aspect of the invention can permit the detection of a specific protein in a mixture of proteins even if the proteins of the mixture are not completely separated from one another.

The method of the present invention may also include the recovery of the stained protein from the solid support for further analysis. Generally, recovery is accomplished by excising gel with stained bands of proteins from the rest of the gel and subjecting the excised part to further processing according to methods which are well known in the art of the invention. With the dyes of the present invention, the time-consuming detection protocols that are currently employed in the art to identify the location of a protein band in a solid support can be avoided. Further, the protocols currently employed in the art require very careful handling of a solid support to avoid undesirable or unacceptable chemical alteration of the desired protein to be recovered from the support; see, e.g., Lujan et al., Meth. Enzymol. 91, 227–236 (1983). The methods made possible by the dyes of the present invention significantly simplify and reduce the risk of damage to the sought protein during recovery of the protein from a solid support. In addition, with a protocol as described in Example 19, the dyes of the invention provide a rapid method to detect desired protein to facilitate further analysis; this avoids the time-consuming procedures usually required for such methods, see Hames, Chapter 6, in Hames and Rickwood, supra.

Because the enhanced hydrophobicity dyes employed in the methods of the present invention permit one to visualize the stained fraction during electrophoresis, it is possible to remove the protein band of interest by observing its location on the gel, creating a liquid reservoir adjacent to the protein band and running the electrophoresis so that the protein band is captured into the reservoir. The details of this advantageous procedure are found in Example 18.

It has been found, surprisingly, with electrophoretically separated proteins stained with some dyes of the invention in solid supports, that suspension of the supports in an acidic aqueous solution (e.g., 5% acetic acid) rapidly and significantly increases the contrast between stained protein and support. This method of enhancing the visibility of protein bands by suspending or exposing the support to an acidic solution (i.e., pH less than about 3) greatly facilitates identification of protein bands in a support and quantification of protein in such bands. See Examples 6, 8, 10 and 12.

The invention further provides a method for sensitively quantitating protein in solution which comprises complexing a Coomassie dye of the invention with the protein in a solution at a pH between about 3.5 and about 8.5, measuring the optical density of the resulting solution, and comparing the optical density with those from standard solutions of known concentrations of protein. With Coomassie dyes available in the art, very low solution pH's, that were often damaging to protein being analyzed, were required for such analyses of proteins in solution. The method of the invention, of quantitating protein in solution, may be useful, for example, in various diagnostic, including medical diagnostic, applications where the concentration of a particular protein in a body fluid is of significance. The method can be applied to a particular, pre-selected protein, that might, for example, have been eluted into solution from a band, identified with a dye of the invention, on a solid support through which a sample of protein (e.g., a sample of a body fluid) had been electrophoresed. See Examples 13 and 14.

Also encompassed by the invention are enhanced hydrophobicity dyes of Formula I (see Page 17, supra) which are derivatives of the known (7-nitrobenz-2-oxa-1,3-diazol-4-yl)amino alkanoic acids of Formula LXXX

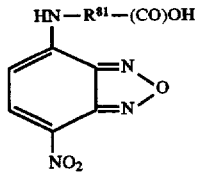

LXXX wherein $R^{81}$ is an alkylenyl group of 1–20 carbons and, more typically, a straight-chain alkylenyl group of formula —$(CH_2)_{aa}$—, wherein aa is 3 to 8. More specifically, these dyes of the invention, referred to herein as derivatives of "NBODY" or "NBODY" dyes, are of Formula LXXXI

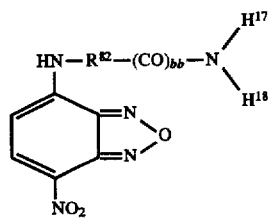

LXXXI wherein $R^{82}$ is an alkylenyl group of 1–20 carbons, bb is 1 or, if the carbonyl group is absent from the compound, 0, and $H^{17}$ and $H^{18}$ are the same or different and each is hydrogen or an hydrophobic group selected from the group consisting of substituted and unsubstituted alkyl, substituted and unsubstituted aryl, and substituted and unsubstituted arylalkyl groups, provided that at least one of $H^{17}$ and $H^{18}$ is an hydrophobic group. More typically, $R^{82}$ will be a straight-chain alkylenyl group of 3 to 8 carbons, bb will be 1, $H^{17}$ will be a group $R^{83}$, which is hydrogen, alkyl of 1–20 carbons, phenyl, or benzyl, and $H^{18}$ will be a group $R^{84}$, which is, independently of $H^{17}$, hydrogen, alkyl of 1–20 carbons, phenyl or benzyl.

In terms of Formula I, $D_1$ includes a moiety of Formula LXXXII

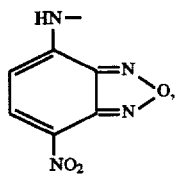

LXXXII and, if $D_1$ is of Formula LXXXII, m is 1, n is 0 and $X_1$ is of Formula LXXXIII

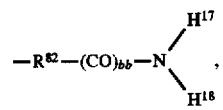

LXXXIII wherein $R^{82}$, $H^{17}$, $H^{18}$, and bb are as defined above. More typically, when $D_1$ is of Formula LXXXII, $X_1$ is of Formula LXXXIV

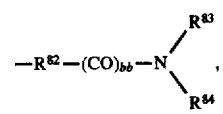

LXXXIV wherein $R^{82}$, $R^{83}$, $R^{84}$, and bb are as defined above.

With reference to Formula II, when $D_1$ is of Formula LXXXII, m is 1, n is 0, and $X_{11}$ has the same definition as $X_1$.

Dyes of the invention of Formula LXXXI are readily prepared. When, in such a dye, bb is 1 and one of $H^{17}$ and $H^{18}$ is hydrogen, the dye can be prepared, as illustrated in Example 40, by reacting an activated ester, such as the N-hydroxysuccinimidyl ester, of the acid of Formula LXXX, and an amine of Formula LXXXIX

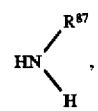

LXXXIX wherein $R^{87}$ has the same definition as $H^{17}$ or $H^{18}$, under standard conditions for preparation of amides from activated esters and amines. The activated ester and amine starting materials for these reactions are available commercially or readily made by a skilled organic chemist.

When, in the dye of Formula LXXXI, both $H^{17}$ and $H^{18}$ are other than hydrogen and bb is 1, the commercially available or readily prepared N-hydroxysuccinimidyl ester of the acid of Formula LXXX is reacted with the commercially available or readily prepared amine of Formula XC

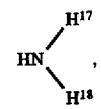

XC under standard conditions for amidation of an acid chloride to provide the dye of Formula LXXXI.

To prepare a dye of Formula LXXXI, wherein bb is 0, the corresponding dye, in which bb is 1, is simply reduced under mild conditions (e.g., using $BH_4^-$ reduction) to convert the carbonyl group to a —$CH_2$— group.

The derivatives of the invention of NBODY are fluorescent. As with the other fluorescent derivatives of the invention, the derivatives of NBODY are employed to stain proteins and then detect the stained proteins by means of the fluorescence imparted by the derivative. Again, as with the other fluorescent derivatives of the invention, a "transilluminator" or a fluoroimager can be employed to detect the proteins made fluorescent by staining with the derivative.

Use according to the invention of dyes of the invention, which are NBODY dyes, is illustrated in Examples 41 and 42.

The following examples are illustrative of the invention but are not intended to limit the scope of the invention.

EXAMPLE 1

Synthesis of Promega Green 1

Coomassie Blue R (Aldrich Chemical Co., Milwaukee, Wis., USA, Catalog No. 20,140-5) (10 g, 0.012 moles) was co-evaporated with pyridine (100 ml) to remove moisture. The residue was dissolved in pyridine (100 ml) and the solution was heated to reflux. After 5 min at reflux, octanoyl chloride (10 ml, 0.059 moles) was added and heating was continued for an additional 15 min. The reaction was followed by thin-layer chromatography (TLC) with 3:1 chloroform:methanol as eluent. TLC indicated conversion to a faster migrating product. The reaction was allowed to cool to room temperature, water (1 ml) was added, and the solution was evaporated to dryness.

The residue was dissolved in 3:1 methanol:water (400 ml) and extracted twice with hexane (2×200 ml). The first hexane extract was back extracted with 3:1 methanol:water (50 ml). The methanol:water solutions were pooled to produce the (stock) solution of Promega Green 1.

EXAMPLE 2

Synthesis of Promega Green 2

Coomassie Blue R (Aldrich, 20,140-5) (10 g, 0.012 mole) was co-evaporated with pyridine to remove moisture. The residue was dissolved in pyridine (50 ml) and the solution was heated to reflux. Acetic anhydride (5 ml, 0.053 mole) was added and reflux was continued for an additional 15 min.

The reaction was followed by TLC with 3:1 chloroform:methanol as eluent. TLC indicated conversion to a slightly faster migrating product. The reaction was allowed to cool to room temperature and the solution was evaporated to dryness. The residue was redissolved in 1:1 methanol:water (100 ml) and re-evaporated.

The residue was re-dissolved in 1:1 methanol:water (600 ml) and extracted twice with hexane (2×300 ml). The first hexane extract was back extracted with 1:1 methanol:water (100 ml). The methanol:water solutions were pooled to produce the (stock) solution of Promega Green 2.

EXAMPLE 3

Synthesis of Promega Green 3

Coomassie Blue R (Aldrich Chemical Co., Milwaukee, Wis., USA, Catalog No. 20,140-5) (10 g, 0.012 moles) was dissolved in pyridine (50 ml) and the mixture was heated to reflux. Lauroyl chloride was added several times over a two-hour interval until a total of 27 ml (0.117 mole) was added.

The reaction was followed by thin-layer chromatography (TLC) with 3:1 chloroform:methanol as eluent. TLC indicated conversion of the blue starting material to a green derivative with little change in mobility. The reaction was allowed to cool to room temperature and the solution was evaporated to dryness.

The residue was dissolved in 2:1 methanol:water (700 ml) and extracted twice with hexane (2×300 ml). The first hexane extract was back extracted with 100 ml 2:1 methanol:water. The methanol:water solutions were pooled to produce the (stock) solution of Promega Green 3.

EXAMPLE 4

Spectral Analyses of Coomassie Blue R and Promega Green 1, 2, 3

The three solutions of Promega Green 1, 2, and 3, from examples 1, 2 and 3 respectively, were diluted approximately 500 fold into a 1:1 solution of methanol:water. The spectra of the resulting solutions and of a 12 µg/ml solution of Coomassie Blue R (in 1:1 methanol:water) were recorded from 700 to 340 nm versus 1:1 methanol:water. This analysis showed that the solution of Coomassie Blue R showed one major absorbing peak in this region of the spectrum with a maximal absorbance at around 590 nm. All of the derivatives gave essentially identical spectra; however, the maximal absorbance of the diluted Promega Green i was about twice that seen for the other derivatives. The derivatives had two peak absorptions in the region of the spectrum scanned, a major peak at around 630 nm and a second peak at around 440 nm. The following absorbances were recorded at the peaks near 630 nm for the three Promega Green dye solutions (diluted 1:500 in 1:1 methanol:water):

| Dye | Absorbance |
| --- | --- |
| Promega Green 1 | 1.66 |
| Promega Green 2 | 1.37 |
| Promega Green 3 | 0.83 |

The spectral (and chromatographic) differences reported here confirm that the original, Coomassie Blue R dye had indeed been derivatized. It is possible that the differences in absorption reflect the variations in the final concentrations of the solutions of the derivatives and not differences in the molar absorbtivities of the derivatives.

EXAMPLE 5

The Use of Promega Green 1 in the Detection of Proteins During SDS-PAGE Electrophoresis Since earlier reports (Schagger, H. et al., supra.) suggested that reduced levels of SDS in the gel components used in SDS-PAGE electrophoresis would improve staining by related dyes, polyacrylamide gels and buffer used to perform this analysis had reduced SDS concentrations.

Solutions for the formation and electrophoresis of proteins were made according to the instructions given in Experiments in Gene Fusions, Silhavy, Berman, Enquist, Cold Spring Harbor Laboratory Press, Cold Spring Harbor, N.Y. with the following changes:

a) The SDS concentration in the upper and lower gel buffer components were reduced to result in a 0.05% final SDS concentration in the gel. Thus, the composition of 4× upper gel buffer was 0.5M Tris-HCl, pH 6.8, 0.2 % (w/v) sodium dodecylsulfate (SDS) and the composition of 4× lower gel buffer was 1.5M Tris-HCl, pHS.8, 0.2 % (w/v) SDS.

b) The SDS concentration in the electrophoretic (electrode) buffer was reduced to 0.04% final concentration. Thus, 4× electrode (anode or cathode) buffer was made by dissolving 60 g Tris base, 288 g glycine, and 8 g SDS dissolved in water and then diluting with water to 5 liters. Another name sometimes used for "electrode" buffer is "running" buffer.

c) The SDS concentration in the 2× sample buffer was reduced to 1% final SDS concentration. Thus, 2× sample buffer was made by mixing 0.5 ml of betamercaptoethanol, 0.25 ml of 0.1% (w/v) bromophenol blue, 1 ml of 10 % (w/v) SDS, 3 ml of water, and 5.3 ml of 2× glycerol buffer. 2× glycerol buffer is made by mixing 12.5 ml of 4× upper gel buffer and 20 ml of glycerol and diluting the resulting solution to 60 ml with water. Another name sometimes used for "sample" buffer is "loading" buffer.

d) Electrophoresis was performed using a BIO-RAD miniprotein II electrophoresis apparatus and gels were poured such that i cm of space was present between the bottom of the loading wells and the separating gel.

In other electrophoresis experiments reported in this application, the buffers used were as described above in this example. In some cases, as in this example, where preparation of a solution of dye in 150 ml of cathode (or electrode) buffer is specified, an amount of stock solution of a dye was first added to 150 ml of cathode buffer and then 125 ml of the resulting solution was used to fill the cathode buffer chamber (which holds 125 ml) in the electrophoresis apparatus. In other cases, where addition of stock solution of dye to the cathode buffer is specified without reference to the volume of cathode buffer or with reference to such volume being "125 ml," the stock solution was added directly to 125 ml of cathode buffer already in the cathode buffer chamber.

The samples used were prepared with Promega Mid-Range Molecular Weight Markers solution (Promega Corp., Madison, Wis., USA, Catalog No. V5231) (referred to hereinafter as "Promega Mid-Range [Molecular Weight] Markers or Standards") diluted into Sample Buffer. Promega Mid-Range Molecular Weight Markers is a solution, at about 0.5 mg/ml, of each of the following proteins as a molecular weight standard: phosphorylase B (apparent molecular weight: 97,400 daltons ("d")), bovine serum albumin (apparent molecular weight: 66,200 d), glutamate dehydrogenase (apparent molecular weight: 55,000 d), ovalbumin (apparent molecular weight: 42,700 d), aldolase (apparent molecular weight: 40,000 d), carbonic anhydrase (apparent molecular weight: 31,000 d), soybean trypsin inhibitor (apparent molecular weight: 21,500 d), and lysozyme (apparent molecular weight: 14,400 d). The dilutions performed resulted in solutions containing 4, 2, 1.5, 1.0, and 0.5 µl of Marker solution per 20 µl of sample solution, thus giving protein concentrations of 2, 1, 0.75, 0.5, and 0.25 µg of each marker band per 20 µl of sample solution. The samples were heated to 95° C. for 10 minutes with occasional vortex treatment in 1.5 ml Eppendorf centrifuge tubes and then centrifuged in an Eppendorf centrifuge for 20 seconds to ensure that the protein in the sample was denatured and well mixed.

Three 10% SDS-PAGE gels were poured as described in the reference above using the alternate solutions above.

After polymerization of the stacking gel, the gel combs used to form the sample wells in the gel were removed and unpolymerized solution in the wells was rinsed from the loading wells with distilled water. The wells were emptied by inversion of the gel and 20 µl of the samples described above were loaded into 5 consecutive dried sample wells in each gel. The Promega Green 1 stock described above was diluted into electrode (cathode) buffer (0.04% SDS w/v final concentration) at a ratio of 0.2, 0.4, and 0.6 ml of dye stock per 150 ml of electrode (cathode) buffer. One of these solutions was used to complete the filling of the sample wells in one gel and then the remaining solution was used to fill the cathode buffer chamber used to run the corresponding gel. The loaded gel was inserted into the electrophoretic apparatus. The cathode chamber was filled with the appropriate solutions described above. The anode chambers were loaded with electrode buffer without dye and electrophoresis was performed at 160 V until a dark dye band which formed during the separation and moved towards the anode began to emerge from the bottom of the gel; this took approximately 1 hour.

A white plastic card was placed behind the gel to allow visualization of the gel without interference from the color in the cathode chamber. During electrophoresis, the protein bands in the lanes containing 2.0 and 1.0 µg of protein per band became visible during the separation and by the end of the run, most of the bands in the lanes containing 0.75 and 0.5 µg of protein per band were visible against an essentially clear background. Slightly easier detection of the bands were observed in the gels containing increased levels of dye, however a corresponding increase in the color in the gel background was seen.

EXAMPLE 6

Enhancement of the Staining of Proteins in SDS-PAGE Gels Stained with Promega Green 1

The gels described above were placed in 5% acetic acid following the termination of the electrophoretic separation. Within one to two minutes the gel developed a light green background but the protein bands dramatically darkened to a green color. All of the protein bands in all the lanes having sample were now visible in all the gels. Again, the color of the background darkened to a greater degree when greater concentrations of dye were used.

Upon allowing the gels to incubate overnight in 5% acetic acid, the stain in the background of the gel was released into the solution. The intensity of the color in the protein bands appeared to darken slightly.

EXAMPLE 7

Use of Promega Green 2 in the Detection of Proteins During SDS-PAGE Electrophoresis The ability of Promega Green 2 to stain proteins during electrophoresis was tested as described above (Example 5) except that 1.0, 2.0, and 3.0 ml of the solution of Promega Green 2 was added separately to individual cathode buffer solutions (150 ml of electrode buffer for each solution). Gels were run as before. The lanes containing 2.0 and 1.0 µg protein per band were visible while the gel was running if a white plastic card was placed behind the gel during electrophoresis.

EXAMPLE 8

Enhancement of the Staining of Proteins in SDS-PAGE Gels Stained with Promega Green 2

The gels above (from Example 7) were placed in 5% acetic acid following termination of the electrophoretic separation. Within 1-2 minutes, all the gels turned light green and the color of the stained bands intensified such that all proteins were visible—even in the lane containing 0.25 µg protein/band.

After overnight incubation, the stain in the gel diffused into the acetic acid solution but the protein bands appeared to have become slightly faded.

EXAMPLE 9

Use of Promega Green 3 in the Detection of Proteins During SDS-PAGE Electrophoresis The ability of Promega Green 3 to stain proteins during electrophoresis was tested as described above (Example 5)

except that 0.2, 0.3 and 0.5 ml of the dye solution of Promega Green 3 was added separately to individual cathode buffer solutions (150 ml of electrode buffer per solution). Gels were run as before. The lanes containing 2.0 and 1.0 µg protein per band were visible while the gel was running if a white plastic card was placed behind the gel during electrophoresis.

EXAMPLE 10

Enhancement of the Staining of Proteins in SDS-PAGE Gels Stained with Promega Green 3

The gels above (Example 9) were placed in 5% acetic acid following termination of the electrophoretic separation. Within 1–2 minutes, all the gels turned light green and the color of the stained bands intensified such that all proteins were visible—even in the lanes containing 0.25 µg protein/band.

After overnight incubation, most of the stain in the gel had diffused into the acetic acid solution, although a greater amount of stain remained in the gel than was seen with Promega Green 1, leading to a darker background color with Promega Green 3.

From these studies (Examples 5–10), it appeared that Promega Green i had the most desirable properties of the compounds tested although all of the derivatives performed well in the enhancement method (Exs. 6, 8 and 10). The enhancement method has not been reported for any other protein dye, including the Coomassie dyes.

EXAMPLE 11

The Use of Promega Green 1 in Polyacrylamide Gels not Containing SDS

A polyacrylamide gel was made containing a 10% separating gel and a 3% stacking gel having 50 mM Tris-HCl pH 8.0 as a buffer. A sample loading solution was made containing Promega Green 1 dissolved in 50 mM Tris-HCl, pH 8.0, 20% glycerol. Samples of bovine serum albumin (BSA) and carbonic anhydrase were added to the sample buffer. The samples were loaded onto the gel and the gel was assembled into a BioRad miniprotean II gel system. An electrode buffer solution of 50 mM Tris pH 8.0 was used to fill the buffer chamber and a voltage of 150 volts was applied to the apparatus. The BSA and carbonic anhydrase samples were seen to migrate through the gel as stained bands that had bound a fraction of the stain in the loading buffer. Therefore, the stain need not be used only in systems containing SDS.

EXAMPLE 12

Development of a Method for the Rapid Enhancement of the Staining of Proteins With Promega Green 1 that Results in Low Residual Color in the Gel As mentioned earlier, it is desirable to be able to quickly visualize proteins in a manner that also results in very little color retention in the gel background so that protein quantitation by methods such as densitometry can be accurately and rapidly performed.

In order to develop such a method, several 10% SDS-PAGE gels made as described in Example 5 were made and loaded with samples made as described therein with the following changes: the sample loading size was reduced to 5 µl; and the solutions were made to contain 1.0, 0.50, 0.25, and 0.125 µg of each protein band of Promega Mid Range Molecular Weight Markers in 5 µl of the sample. Each gel was loaded such that duplicate panels of samples containing the various concentrations of protein were present in 4 consecutive lanes. The gels were run as described above and the gel was cut between the duplicate sample panels. A gel segment containing one panel was placed in each of the following solutions: 30 ml of 2% glacial acetic acid (A); 30 ml of 2% glacial acetic acid in 10% methanol (B); 2% glacial acetic acid in 20% methanol (C); 2% glacial acetic acid in 30% methanol (D); 30 ml of water (E); 30 ml of 10% methanol (F); 30 ml of 20% methanol (G); and 30 ml of 30% methanol (H). The solutions were incubated with the gel segments for 10 minutes at room temperature and gently rotated at 40 rpm to prevent settling of the gel segments in the containers. After this time, the original solutions were removed and the following liquids were applied to the gel segments: 30 ml of 2% acetic acid was applied to the segments treated with A and E; 30 ml of 2% acetic acid in 10% methanol was applied to the segments treated with B and F; 30 ml of 2% acetic acid in 20% methanol was applied to the segments treated with C and G; and 30 ml of 2% acetic acid in 30% methanol was applied to the segments treated with D and H. The segments were then incubated for 60 minutes at room temperature with gentle rotation (40 rpm).

After this time, the segments first treated with solution E, F, G, and H all showed less background staining than their corresponding segments treated with A, B, C, and D. In addition, all protein bands were visible in all gel segments -demonstrating that less than 125 ng of protein in a band can be detected using these procedures. In addition, although the gels were slightly reduced in size, those treated with increasing concentrations of methanol had less background staining regardless of whether the gel segment was first treated with a solution containing acetic acid. In particular, the segment treated with solution set H had very little background staining remaining and could be used to quantitate the protein bands present.

Protocols using other dyes that have been developed for the sensitive detection of protein sometimes employ the incubation of the gel in solutions containing the stain followed by incubation of the gel in solutions lacking the stain. In order to determine if such a protocol could be used to allow even lower levels of protein to be detected using Promega Green 1, the following study was performed.

Three SDS-PAGE gels were constructed as described in Example 5. Samples of Promega Mid-Range Molecular Weight Markers were made and treated as described in that Example with the following changes: the sample sizes applied to the gel were 5 µl; and individual samples were made to contain 1.0, 0.5, 0.25, 0.125, 0.0625, 0.0312, and 0.0156 g of each protein band in the 5 µl samples. Samples were loaded into the gels and subjected to electrophoresis as described in Example 5. After electrophoresis, the gels were incubated in 50 ml solutions containing 30, 40 or 50% methanol and a 1:5000 dilution of the Promega Green 1 Stock solution for 10 minutes with gentle agitation. After this time, the liquids were removed and the following solutions were applied to the gels: the gel treated with the 30% methanol solution above was treated with 50 ml of 30% methanol, 2% acetic acid containing a 1:10,000 dilution of Promega Green i stock; the gel treated with the 40% methanol solution was treated with 50 ml of 40% methanol, 2% acetic acid containing a 1:10,000 dilution of Promega Green 1 stock; and the segment treated with the 50% methanol solution was treated with 50 ml of 50% methanol, 2% acetic acid containing a 1:10,000 dilution of Promega Green 1 stock. The gels were then gently rotated at 40 rpm at room temperature for 10 minutes.

After this time, the solutions were removed and 50 ml solutions corresponding to that removed, but lacking the dye, were applied and the gels were gently rotated at 40 rpm at room temperature for 10 minutes. After 60 minutes, all the gels showed very little background staining and all the bands of protein in the lane containing 62.5 ng of protein per band was visible. This protocol then can be used to detect very small amounts of protein with little background staining.

EXAMPLE 13

The Effect of Solution pH on the Absorption of Promega Green 1 in the Presence and Absence of Protein The effect of solution pH on the absorption of Promega Green 1 in the presence and absence of added protein was studied by dilution of Promega Green 1 solution at a ratio of 1:1000 (v/v) into various solutions containing 0 or 100 µg of protein (bovine serum albumin (BSA)) per ml of liquid. The solutions tested were highly acidic (1N HCl), moderately acidic (2% acetic acid), weakly acidic (50 mM ammonium acetate pH 4.0), weakly basic (50 mM ammonium bicarbonate pH 7.8), and strongly basic (500 mM Tris base). The absorption spectra of the solutions were measured from 700 to 340 nM and the peak absorbances are reported below.

| solution | Protein Absent | | Protein Present | |
|---|---|---|---|---|
| | max | ABS | max | ABS |
| strongly acidic | 649 nm | 0.27 | 641 nm | 0.39 |
| moderately acidic | 631 nm | 0.83 | 635 nm | 0.98 |
| weakly acidic | 636 nm | 0.49 | 638 nm | 0.25 |
| weakly basic | 636 nm | 0.49 | 637 nm | 0.26 |
| strongly basic | 637 nm | 0.22 | 637 nm | 0.128 |

These results show that the absorbance of the dye in the absence of protein displays a dependence on the pH of the solution, indicating that the dye can be used as a wide range pH indicator.

In addition, the dye protein complex displays a different absorption than the dye alone. The effect can result either in an increased level of absorption as is shown in strongly acidic solutions, or a decrease in absorption as is shown for weakly acidic or basic solutions. Thus the dye can be used in protein quantitation formats that can measure the presence of protein by either measuring an increase or decrease in the dye protein complex compared to the dye itself.

EXAMPLE 14

Development of a Sensitive Solution Protein Quantitation Assay Using Promega Green 1

In order to conclusively determine a format for the sensitive quantitation of protein in solution using Promega Green 1, Promega Green 1 stock solution was diluted at ratios of 1:250 (v/v) and 1:1000 (v/v) into 0.5M tris base containing 0, 5, 10, 20, 40, 60, 80, and 100 µg protein (BSA) per ml of solution. After incubation of the solutions for 3 hours at room temperature, the absorption of the solutions at 636 nm was measured.

| Protein concentration | Absorption at 630 nm Dilution of dye | |
|---|---|---|
| (µg/ml) | 1:1000 | 1:250 |
| 0 | 0.079 | 0.543 |
| 5 | 0.069 | 0.515 |
| 10 | 0.059 | 0.472 |
| 20 | 0.051 | 0.427 |
| 40 | 0.048 | 0.386 |
| 60 | 0.047 | 0.358 |
| 80 | 0.044 | 0.342 |
| 100 | 0.043 | 0.317 |

These results show that the above format can be used to determine the protein content of solutions at very sensitive levels.

EXAMPLE 15

The Use of Promega Green 1 for the Quantitation of Proteins Separated by SDS-PAGE Electrophoresis The use of Promega Green 1 for the quantitation of proteins separated using SDS-PAGE electrophoresis was demonstrated in the following way. A 10% SDS-PAGE gel was made as described in the Example 5. Promega Mid-Range Molecular Weight Standards were diluted into loading buffer to produce solutions containing 2.0, 1.0, 0.5, and 0.25 µg of protein per band in 5 µl of solution. Duplicate 5 µl solutions of each of these solutions were loaded into 1 of the 10 sample wells in the gel after the solutions were heated at 95° C. for 10 minutes. The gel was then electrophoresed at 160 V until the running dye just eluted from the bottom of the gel. The gel was destained, and signal from stained protein enhanced, for 90 minutes in 30% methanol, 4% acetic acid.

One of the pair of duplicate bands for the 97.4, 66.2, 55.0 and 42.7 kilodalton standards from the lanes containing 2.0, 1.0, 0.5, and 0.25 µg of protein per band were excised with a razor blade as were two control gel segments from regions of the gel not containing protein. The excised segments were placed in individual 1.5 ml Eppendorf tubes containing 2% SDS and allowed to incubate at room temperature for 72 hours. After this time, the solutions were removed from the extracted segments and acetic acid was added to 2% (v/v) final concentration. The absorption of the solutions at 630 nm was then measured.

| Protein amount | | | Absorbance at 630 nm Protein Sample | | | |
|---|---|---|---|---|---|---|
| (µg/band) | Blank | Regions | 97 kD | 66 Kd | 55 Kd | 43 Kd |
| 0 | .018 | .015 | | | | |
| 0.25 | | | .032 | .052 | .053 | .042 |
| 0.50 | | | .053 | .074 | .063 | .064 |
| 1.00 | | | .083 | .138 | .105 | .126 |
| 2.00 | | | .128 | .192 | .138 | .195 |

These data show that Promega Green 1 can be used to quantitate proteins separated by SDS-PAGE electrophoresis. The method is very sensitive, allowing as little as 250 ng of protein to be measured quantitatively.

EXAMPLE 16

The Use of Promega Green 1 for the In-Situ Staining of Proteins During Transfer to Immobilizing Supports The use of immobilizing supports such as nitrocellulose, nylon, glass or polyvinyl difluoride has become very common in the immunochemical or sequence analysis of proteins. In order to demonstrate the use of Promega Green 1 for the staining of proteins during the transfer of proteins to such supports, an SDS-PAGE gel was made, loaded and run as described in Example 15. A segment of Immobilon P™ from Millipore Company was wetted in 100% methanol for 30 seconds then equilibrated in transfer buffer (25 mM tris base, 192 mM glycine) for two minutes. Two Whatman 3 mM sheets were soaked in transfer buffer and these components were then used to construct a transfer sandwich composed of one sheet of Whatman paper, the SDS-PAGE gel, the Immobilon sheet, and the final sheet of Whatman. The sandwich was placed in a Hoeffer transfer apparatus and oriented in the apparatus such that the Immobilon side of the sandwich was oriented toward the positive electrode. The apparatus was placed at 4° C. and 10 V were applied to the apparatus for 30 minutes then the voltage was increased to 30 V for an additional 120 minutes.

The transfer apparatus was then disassembled and the surface of the Immobilon membrane that had been in contact with the gel displayed visible protein bands in the lanes that had contained 2.0 and 1.0 µg protein per band. The Immobilon membrane was then soaked in 45% methanol, 5% acetic acid for 2 minutes. This procedure enhanced the staining of the proteins transferred to the Immobilon membrane such that the protein band at all concentrations became easily visible. These data demonstrate that the dye can be used to stain proteins during electrophoretic transfer to immobilizing supports and that the enhancement seen in gels can also be demonstrated with protein transferred to such supports.

EXAMPLE 17

The Use of Promega Green 1 in the Recovery of Proteins Separated by Gel Electrophoresis The Use of Promega Green 1 in the recovery of proteins separated by gel electrophoresis was demonstrated in the following way. An 8% SDS-PAGE gel was prepared as described above and loaded with Promega Mid-Range Molecular Weight Markers at a concentration of 4 µg of each protein per lane. The gel was run at 160 V with 200 µl of octyl Coomassie (Promega Green 1) stock solution in the cathode buffer (125 ml).

After electrophoresis, the gel segments containing the 97, 66, 55, 43, and 40 kilodalton proteins were excised from four consecutive lanes, minced, and placed in individual 1.5 ml Eppendorf tubes containing 0.5 ml of 50 mM ammonium bicarbonate pH 7.8 containing 0.02% SDS (w/v). The tubes were then incubated at 50° C. for 14 hours.

After that time, the tubes were spun for 1 minute in a microfuge to pellet the minced acrylamide and 0.47 ml of the supernate was removed to new 1.5 ml tubes. Two of the four solutions from each of the eluted protein samples were dried in a Speed-Vac, the other pair was first ultrafiltered through a 5000 dalton cut-off Milligen centrifugal concentrator by centrifugation in a microfuge for 30 minutes. These concentrated solutions were then dried in a Speed Vac.

The dried samples were resuspended in 25 µl of 1× loading buffer and heated at 95° C. for 10 minutes. These samples were then loaded in two 15-well, 0.75 mm 10% SDS-PAGE gels made as above. The gels were then run at 160 V with 200 µl of Promega Green 1 stock solution in the cathode buffer (125 ml). After electrophoresis, the gel was enhanced for 1 hour in 30 % methanol, 4% acetic acid. At this time in the gel, the expected protein bands could be seen in the lanes. These data demonstrate that the dye can be used in the recovery of proteins separated by gel electrophoresis.

EXAMPLE 18

The Use of Promega Green 1 for the Recovery of Protein Separated by Gel Electrophoresis Using a Novel Recovery Method Because Promega Green 1 can be used to stain protein during electrophoretic separations, we determined that proteins separated by gel electrophoresis can be recovered into a liquid reservoir placed in the gel. This is possible only with in-situ stained proteins because it would not be obvious where to place the liquid reservoir otherwise.

Accordingly, an 8% SDS-PAGE gel was made, loaded and run as described in the preceding example. After the run was complete, one of the glass plates encasing the gel was removed and 1.0×0.3 cm slots were excised from the gel immediately below the 97, 66, 40, and 31 kilodalton standards The gel was then placed in a flat bed electrophoresis apparatus which had its buffer chambers filled with 25 mM tris base, 192 mM glycine (electrode buffer) to the level of the central, raised portion of the apparatus. The gel was placed in the apparatus such that the acrylamide gel above the remaining glass plate was filled with electrode buffer. The slots were also filled with electrode buffer and electric connection was made between the gel and the buffer chambers by use of Whatman 3 mM paper wicks soaked in transfer buffer and then 160 V was applied to the apparatus for 2 minutes. After this, the buffer in the slots was removed and placed in 1.5 ml Eppendorf tubes, the slots were refilled with fresh electrode buffer and the voltage was reapplied. This cycle was repeated 3 more times and the samples from identical slots were pooled and dried in a Speed-Vac.

After drying, the samples were redissolved in 25 µl of 1× sample buffer. A 10% SDS-PAGE gel was made as described in Example 5. The samples were loaded onto the gel and electrophoresis was performed as described in that example. After the run was complete, the staining was enhanced in 30% methanol, 4% acetic acid.

Analysis of the gel showed that the desired protein bands had been captured by this method. Thus, this protocol can be used to isolate proteins electrophoretically without the need to: stain the gel following electrophoresis; destain the gel; re-equilibrate with SDS; or electroelute the protein by use of special electrophoresis equipment. This method specifically allows this advantage due to the fact that the separating protein bands are visible during the initial electrophoretic separation.

EXAMPLE 19

The Use of Promega Green 1 in the Analysis of Partial Proteolytic Products of a Protein The comparison of proteins by analysis of the products of partial proteolysis using SDS-PAGE electrophoresis has been reported extensively in the literature. This analysis, termed Cleveland analysis, can provide important information on many different types of covalent changes that can occur on proteins.

To determine if the dyes can be used advantageously in such analysis, the following study was performed.

An 8% SDS-PAGE gel was made as described in Example 5. A 5 µl sample of 1× loading buffer containing 4 µg of Bovine serum albumin previously heated at 95° C. for 5 minutes was placed in several of the wells and electrophoresis was performed as described in Example 5.

A second 1.0 mM thick 16% SDS-PAGE gel was made as described in Example 5.

After electrophoresis, segments of the gel containing the BSA sample were excised by use of a razor blade and loaded into three of the sample wells of the second, 16 % gel. Then, 20 µl of 1× loading buffer containing 0.5 µg of Endoprotease Glu C, 0.5 µg of Endoprotease Lys C and 0.1 µg of Alkaline Protease, respectively, was added to individual wells containing the gel slices. Also, 5 µl of a solution of 4 µg of BSA in 1× loading buffer that was previously heated to 95° C. for 15 minutes was placed in a second set of three wells. To each of these three samples was added individual 20 µl solutions containing 0.5 µg of Endoprotease Glu C, 0.5 µg of Endoprotease Lys C, or 0.1 µg of Alkaline Protease, respectively. The gel was then run at 50 V with 200 µl of stock solution of octyl Coomassie (i.e., Promega Green 1) present in the cathode buffer (125 ml). When the dye band reached the interface between the stacking gel and the separating gel, the voltage to the apparatus was shut off for 30 minutes, then the voltage was reapplied, adjusted to 160 V and electrophoresis continued until the tracking dye emerged from the bottom of the gel. At this point, the staining was enhanced using 30% methanol, 4% acetic acid. The partial proteolytic pattern of the digested samples was readily apparent in a very short period of time.

These results indicate that the use of Promega Green 1 does not interfere with Cleveland type protein analysis. In addition, they indicate that the dye simplifies such analysis by eliminating the staining, destaining and re-equilibration steps normally needed to perform such analysis.

EXAMPLE 20

Synthesis of Derivatives of Acid Blue 25

Acid Blue 25 (Aldich Chemical Co., Milwaukee, Wis., USA, Catalog No. 21,068-4) (3.0g, 72 mmoles) was co-evaporated with pyridine (50 ml) to remove moisture. The residue was dissolved in pyridine (100 ml) and the solution was heated to reflux. After reflux was achieved, octanoyl chloride (2.5 ml, 2 equivalents) was added dropwise. Reaction occurred immediately as indicated by the color of the mixture changing from blue to brown-red. After reaction for five minutes, thin-layer chromatography of the reaction mixture on silica gel plates using a mixture of 4:1 chloroform:methanol as a solvent indicated that the mixture was comprised primarily of two faster migrating products and some starting material. Three additional equivalents of octanoyl chloride were added to the reaction mixture and the mixture was refluxed an additional five minutes. Methanol was added to destroy excess acid chloride and then the final material dried by evaporation in a rotary evaporator.

A small amount of this dried material was dissolved in 2 ml of methanol for use as a stain mixture ("unpurified" deriavtized Acid Blue prep).

The remaining material was azotropically distilled two times with toluene to remove pyridine contamination, dried and subsequently fractionated to test as purified stain species.

EXAMPLE 21

Fractionation of Derivatives of Acid Blue 25

The purified material from Example 20 was redissolved in chloroform:methanol (10:1) and placed on a 300 g silica gel column using 10:1 chloroform:methanol as an eluant.

Fractions were collected and tested for their dye composition by TLC chromatography on silica gel plates using 4:1 chloroform:methanol as a solvent. The faster moving, major product, which was purple in color, was collected and dried using a rotary evaporator.

The elution solvent, for the silica gel column, was changed to 4:1 chloroform:methanol. Additional fractions were collected. The fractions were tested for their dye composition by TLC as described above and those containing the second, slower major product (which was cherry red in color) were pooled and dried.

EXAMPLE 22

The Use of Unpurified Acid Blue 25 Derivatives in the Detection of Proteins During SDS-PAGE Electrophoresis Three gels were prepared as described in Example 5.

Promega Mid-Range Molecular Weight Standards were diluted into the 2× sample buffer described in Example 5 diluted to 1× to produce sample containing 2, 1, 0.75, 0.5, 0.4, 0.3, 0.2 and 0.1 µg of each protein species present in the standard mix per 10 µl of solution. Ten µl of each solution was loaded into lanes of the three gels, and they were placed into three separate Bio-Rad Miniprotean II gel apparati (Bio-Rad, Richmond, Calif., USA) with the cathode solutions containing 1.0, 0.75, or 0.5% (v/v) of the derivatized Acid Blue 25 preparation (unpurified). The samples were then fractionated within the gels by application of 15 mA of current per gel. Protein bands became visible to a detection limit of at least 0.4 µg of protein per band as red bands migrating through the gel as the sample separated in the gel while electrophoresis was being performed. Thus, the modified dyes allow the visualization of protein during electrophoresis.

EXAMPLE 23

Comparison of Unpurified Acid Blue 25 Derivatives and Unmodified Acid Blue 25 in the Detection of Proteins During SDS-PAGE Electrophoresis Two gels were prepared as described in Example 5.

Promega Mid Range Molecular Weight Standards were diluted into the 2× sample buffer described in Example 5 diluted to 1× to produce samples containing 1 µg of each protein per 10 µl of solution. The solution was heated at 95° C. for 5 min. The solution was allowed to cool to room temperature and 20, 10, 5, and 2.5 µl of the solution was loaded into separate loading wells of the two gels. The gels were assembled in Bio-Rad Miniprotean II gel apparati and the cathode buffer solution for one of the gels contained 1% (v/v) of the Acid Blue 25 derivative solution mixture (unpurified) described in Example 20 while the cathode buffer for the other gel contained 0.01% (w/v) of unmodified Acid Blue 25. The samples was then separated by application of current to the gel at 15 mA per gel. Protein bands were seen at levels as low as 0.25 µg per protein species in the gel where unpurified derivatives of Acid Blue 25 were placed in the cathode buffer while no protein bands were seen in the gel having underivatized Acid Blue 25 placed in the cathode buffer. Thus, the derivatives of Acid Blue 25 allowed proteins to be visualized as they fractionated in SDS-PAGE gels while the starting dye material (underivatized Acid Blue 25) did not.

EXAMPLE 24

The Use of Purified Acid Blue 25 Derivatives in the Detection of Proteins During SDS-PAGE Electrophoresis Gels were prepared as described in Example 5.

Promega Mid-Range Molecular Weight Standard was diluted to produce solutions containing 1000, 800, 600, 400, 200, and 100 ng of each protein per 10 µl of solution by dilution into 1× loading solution (prepared by dilution of the 2× loading solution described in Example 5). Ten µl samples of these solutions were loaded into the gels and one gel was assembled into one of two Bio-Rad Miniprotean II gel apparati.

The purified dye derivatives which were obtained from the reaction of Acid Blue 25 with octanoyl chloride followed by silica gel column chromatography (Examples 20 and 21) were dissolved in 100 ml of water:methanol (1:1, v/v) and these solutions were added to the cathode buffers of the two gels at 2% (v/v) and 1% (v/v) for the redissolved upper (purple) and lower (cherry red) dye derivative, respectively. The samples were fractionated by electrophoresis at 20 mA per gel. After 30 min. the proteins began to separate in the separating gel and essentially all the bands could be seen for all protein species at every protein concentration applied to the gel. This indicates that either major dye derivative made from Acid Blue 25 could be used for sensitive detection of protein as it moves in SDS-PAGE gels.

EXAMPLE 25

Synthesis of Dansyl Chloride Derivatives

Five separate solutions were prepared by adding 30 mg of dansyl chloride in 1.5 ml of acetone to 8.5 ml of 100 mM sodium phosphate buffer, pH9.5. To each of these solutions was added i ml of a solution of one of the following amines, at 0.15 mmole/ml in acetone: n-butyl amine, sec-butyl amine, tert-butyl amine, n-octyl amine, and n-dodecyl amine. A separate reaction was also performed in which 30 mg of dansyl chloride in 1.5 ml of acetone was added to 8.5 ml of 100 mM sodium phosphate buffer, $pH_{9.5}$ and, to this, 1.0 ml of acetone and 20 mg of solid ammonium sulfate were added. The reactions were allowed to incubate 15 min at room temperature. During this time, the solutions developed the following characteristics:

| REACTION | APPEARANCE |
| --- | --- |
| n-dodecyl amine | heavy yellow precipitate |
| n-octyl amine | white milky solution |
| ter-butyl amine | yellow solution |
| all others | yellow solution |

The reaction solutions were diluted to 15 ml with acetone and allowed to incubate overnight.

Samples of the solutions were spotted onto a silica gel thin layer chromatography plate and developed with chloroform. The thin layer chromatography plate was developed and the fluorescent species were visualized by laying the plate on a transilluminator. Many of the species observed were present in all of the samples. However, each reaction also displayed a unique, major species, which represented the desired derivative. Due to the fact that the unique species altered in mobility in a regular manner, depending on the amine used in the reaction, and were not present in the control reaction (run with ammonium sulfate), these were determined to be the desired derivatives.

EXAMPLE 26

Purification of Dansyl Chloride Derivatives

Two ml of each of the reaction solutions of Example 25 were separately spotted preparatively onto a 20×20 cm silica gel thin layer chromatography (TLC) plate. Following development using chloroform and visualization of the fluorescent species separated on the plates by observation of the plates on a transilluminator, the silica gel in the regions of the plates containing the unique chemical species was removed from the plate by scraping the plate with a razor blade and the gel was transferred to 15 ml tube and eluted with 10 ml of ethanol. Following overnight elution, 3 µl of the eluate was applied to a 5×20 cm silica gel plate and developed with chloroform. Visualization of the fluorescent species fractionated on the second plate indicated that the derivatives had been purified.

Samples of the eluates from purification of the derivatives were diluted 20-fold with ethanol and the absorption of the resulting solutions from 400 to 220 nm was measured. The absorption of the solutions at 328 nm was used as an indication of the concentration of the derivative in the staining studies in Example 27.

EXAMPLE 27

Detection of Protein Post-Electrophoretically Using Purified Dansyl Derivatives

Several SDS-PAGE minigels were made as described in Experiments with Gene Fusions, Silhavy, Berman, Enquist, supra, using the SDS concentrations described by the authors. Samples of Promega Mid Range Molecular Weight Standards were diluted into the loading solution described in the reference above to produce solutions containing 200, 100, 50, 25, and 12.5 ng of each protein species in 10 µl of solution. These solutions were loaded onto the gels and the samples were fractionated in the gels by application of 10 mA per gel until the tracking dye for the samples reached the bottom of the gel. The gels were then rinsed 1 min in distilled water, 15 min in 10% trichloracetic acid (w/v), and then for 15 min in 10% methanol (v/v). The gel segments, approximately 5×6 cm containing the fractionated standard, were then transferred to a 2% ethanol solution (50 ml) containing 0.05 $OD_{328}$-equivalent of each of the dansyl derivatives (see Example 26). After 15 min at room temperature, the gels were observed on a transilluminator visually and photographed using a camera loaded with Polaroid Type 667 film (Polaroid Corp., Cambridge, Mass., USA) and using a Tiffen 40.5 F15 orange filter (Tiffen Manufacturing Co., Happauge, N.Y., USA) At this point, all of the standard bands fractionated on the gel stained with the octyl dansyl derivative were easily visualized in the photograph of the gel and several of the standard protein bands of the 200 and 100 ng samples in the gel stained with the dodecyl dansyl derivative were visible. No staining was seen with the other derivatives.

The gel segments were returned to their respective staining solutions and were incubated overnight. The following morning, all of the gel segments were again visualized on the transilluminator and photographed as described above. At this point, no bands were seen in the gels stained with the control dansyl amine solution (formed by reaction of the dansyl chloride with ammonium sulfate) or the three butyl dansyl derivatives. All of the protein bands of the standards fractionated in the gels stained with the octyl and dodecyl dansyl derivatives were easily visible. However, the staining of the bovine serum albumin and ovalbumin proteins with the octyl dansyl stain appeared to become somewhat fainter after the overnight incubation. In general, relatively equivalent staining of bands was obtained as determined by the strength of the fluorescent signal observed for the various fractionated species. Thus this data indicate that the derivatives do not detect proteins at an equivalent sensitivity but that the detection limit seen-and the rate at which staining will take place-will be dependent upon the particular derivative used. In addition, these data indicate that the octyl and dodecyl derivatives of dansyl are much better stains compared to the amino or butyl derivatives of this molecule.

EXAMPLE 28

Synthesis of Additional Dansyl Derivatives

To each of several 15 ml tubes containing 27 mg (0.1 mmole) of dansyl chloride in 1 ml acetone was added 50 µl of n-butyl amine, n-hexyl amine, n-octyl amine, and n-decyl amine. To each of two additional tubes was added 100 mg of n-dodecyl amine and ethyl p-amino benzoic acid, respectively. After 1 min at room temperature, the following observations were made: The color of the butyl, hexyl, octyl, decyl, and dodecyl reactions changed from an orange color to a yellow color and a precipitate formed in the decyl and dodecyl reactions. No color change was observed in the ethyl p-amino benzoic acid reaction and 50 µl of 10M NaOH and 100 µl of water were added to this reaction mixture. At this point the ethyl-aminobenzoic acid solution changed from the original orange color to a light yellow color. Samples of the solutions were spotted on silica gel thin layer chromatography plates and developed using chloroform. Observation of the plate on a transilluminator indicated that each of the above reactions produced a new chemical species having a unique mobility. The species were then purified by silica gel thin layer chromatography and recovered as described in Example 26. Samples of the purified eluates were rechromatographed and visualization of the fluorescent species in the samples indicated that the unique fluorescent species had been purified. The eluates were each diluted to 50 ml with ethanol before further studies were performed.

EXAMPLE 29

Detection of Fractionated Protein in SDS-PAGE Gels Using Dansyl Derivatives Made in Acetone Several 15-well, SDS-PAGE minigels were poured as described in Example 27 and loaded with Promega Mid Range Molecular Weight Standards diluted as described in Example 27 to provide samples containing 1000, 300, 100, 50, 25, 12.5, and 6.25ng of each protein per band in separate lanes of the gel. The samples were fractionated by application of 20 mA per gel until the tracking dye reached the bottom of the gel. All the gels were placed in 10% trichloroacetic acid for 5 min and then incubated for 10 min in 10% (v/v) methanol. The gels were then incubated in a 10% methanol solution containing 2% (v/v) of the derivative eluates (dissolved in 50 ml ethanol) described in Example 28. The gels were transferred to a transilluminator and both visualized and photographed after two hours of staining. The following observations were made. Only the lanes containing 1000 and 300ng of protein per band were visible in the gel incubated with the n-butyl dansyl derivative. The lanes containing the 1000, 300, 100, 50, 25ng per band were visible in the gel incubated with the n-hexyl derivative as were some of the bands in the 12.5 ng per band lane. Essentially equivalent results, but with lower fluorescence intensities, were seen in the gel stained with the n-octyl derivative. Faint visualization of the 1000, 300, 100, 50 and 25 ng bands of the standard were seen for the bands present in the gels stained with the decyl derivative but detection of bands only to 300 ng per band was seen with the dodecyl derivative. The gel stained with the p-aminobenzoic acid ethyl ester derivative showed good staining with detection of bands at a level as low as 25 ng of protein per band.

After overnight incubation in the stain solutions, the gels were re-observed and rephotographed. The results obtained were essentially the same as above, however increased detection sensitivity was seen with the decyl and particularly with the dodecyl derivatives, such that at least some of the bands present in the lanes containing 12.5 ng of protein per band could be visualized.

The gels were then placed in 1% acetic acid to remove any unbound stain and rephotographed after three hours of incubation in this solution at room temperature. Increased detection sensitivity was observed with the decyl and dodecyl derivatives, such that most of the protein species present in the lanes containing 6.25 ng of protein per band were visible for the decyl and dodecyl derivatives.

Thus the derivatives made in acetone, which were made with less expenditure of dansyl to unproductive derivatives, were capable of staining proteins as well as were the original derivatives. In addition, these results again demonstrated that there was a correlation between the type of derivative tested and the staining results which were achieved with the derivative.

EXAMPLE 30

Optimization of Post-Electrophoretic Staining with Dodecyl Dansyl Stain

In order to determine if alternative staining conditions would improve the detection of protein by fluorescent staining with the dodecyl dansyl stain, the following experiment was performed. Two 12% SDS-PAGE minigels from Bio-Rad Corporation were used to fractionate samples of diluted Promega Mid-Range Molecular Weight Standards which were loaded into alternate lanes of the gel to produce protein bands containing 25 and 5 ng of each protein per band in adjacent lanes. The gels were run as recommended by the manufacturer in Bio-Rad Miniprotean II electrophoresis units and sliced to produce two lane segments containing one lane each of the 25 and 5 ng sample lanes. One slice was placed in each of the following solutions (50 ml) followed by incubation of the segment in a second 50 ml of the solution containing 200 µl of dodecyl dansyl derivative solution (in 50 ml ethanol) of Example 28: distilled water; 1% acetic acid; 1% trichloroacetic acid; 5M sodium chloride; 0.5M Tris base; 0.5M ammonium bicarbonate, pH 5.0; 2M Tris pH8.0; 0.05M sodium hydroxide; and 10% ethanol. The gels were allowed to stain overnight at room temperature and then were observed on a transilluminator to allow visualization and photography of the fluorescently stained bands as described in Example 27. The gels incubated with the stain dissolved in 1% acetic acid and 0.5M ammonium bicarbonate, $pH_{5.0}$ displayed fluorescent protein bands in the lane containing 25 ng of protein per band, while that incubated with the stain in 2M tris pH 8.0 showed much weaker staining. No other staining solution allowed visualization of the fractionated protein species at this point. The gel segment stained in the solution of 1% trichloroacetic acid showed neither protein detection nor background staining while all of the other solutions displayed at least background staining. It was thought that this is due to an inability of the particular stain derivative used to fluoresce under the highly acidic condition produced in the trichloroacetic acid solution.

In order to determine if the stain remained intact in these solutions and to standardize the conditions for the stains, the gel segments were then incubated in 50 ml of distilled water. After 1 hr, the segments were re-observed and re-photographed. Staining was seen in the gels that had been stained in solutions of 1% acetic acid, 1% trichloroacetic acid, 2M Tris ph8.0, and 0.5M ammonium bicarbonate, pH 5.0. Of these, those stained in solutions of 1% acetic acid and trichloroacetic acid showed greater fluorescence. Thus, staining sensitivity is dependent upon staining conditions and mildly acidic conditions appear to improve the sensitivity of staining.

EXAMPLE 31

Optimization of Staining with Dodecyl Dansyl Stain

Since the experimentation of Example 30 indicated that staining of proteins with dodecyl dansyl stain was possible, and since fixation has been reported to allow staining to be performed, the following experiment was performed to determine if a combination of a fixing step and a staining step using acetic acid/ethanol solutions could improve detection. Two 12% SDS-PAGE gels were run with diluted Promega Mid Range Molecular Weight standard to produce samples of proteins at 20, 10, and 5 ng of protein per band present in the gels. The gels were made as in Example 27 and proteins were fractionated on the gels in a BioRad Miniprotean II gel system as recommended by the manufacturer. The gels were cut to produce segments of gel containing three lanes of samples containing one lane each of the protein concentrations described above and placed for 15 min in 50 ml of one of the following fixative solutions: 30% ethanol, 20% acetic acid; 40% ethanol, 10% acetic acid; 40% ethanol, 20% acetic acid; 50% ethanol, 10% acetic acid; and 50% ethanol, 20% acetic acid. After the 15 min incubation, the gels were transferred into another 50 ml of the same fixative solution containing 50 µl of dodecyl dansyl stain solution (in 50 ml ethanol, Example 28). After 3 hrs., the segments were placed in 50 ml of 50 mM Tris-Cl, pH8.0, for 5 min and then were visualized on a transilluminator and photographed. All of the protein bands for the gel segments stained in solutions containing either 30 or 40% ethanol and 10 or 20% acetic acid were faintly visible in the gel segments.

After visualization, the segments were returned to their respective staining solutions and allowed to incubate overnight. The following morning, the segments were visualized and photographed directly on a transilluminator without prior incubation in a different solution. All protein bands at all concentrations were easily visible in the photographed gels. These results indicate that detection of protein at levels at least as low as 5 ng of protein per band can be achieved with this stain.

EXAMPLE 32

In-gel Staining with Dodecyl Dansyl Stain

In order to determine if in-gel staining with dodecyl dansyl stain could be performed, a gel containing the concentrations of reagents in the gel buffers and running buffers listed in Example 5 was made and run as described in Example 5 with two exceptions: 1) dodecyl dansyl stain (in 50 ml ethanol, Example 28) was added to the cathode buffer at 0.1% (v/v) instead of Promega Green 1; 2) Promega Mid-Range Molecular Weight markers were diluted into 1× loading buffer as described in Example 5 and were loaded on the gel to produce lanes containing each protein at concentrations from 1000 ng/lane to 3.1 ng/lane. Following electrophoresis, the gel was placed directly on a transilluminator and visualized and photographed as described above. Protein bands were seen for many of the heavier molecular weight species in the fractionated proteins present in the gel at concentrations as low as 12.5 ng of protein per band; however, staining of the protein species with mobilities allowing them to migrate more than halfway through the gel were not easily detected. Thus, staining while the gel is running can be performed with the dodecyl dansyl stain and is particularly favorable for protein species with low mobilities.

EXAMPLE 33

Synthesis of Dodecyl and Octyl Derivatives of MDPF

Solid MDPF, 2-methoxy-2,4-diphenyl-3(2H)furanone, (FLUKA Chemical Co., Ronkonkoma, N.Y., USA), 18 mg. in 450 µl of dimethyl formamide (i.e., N,N-dimethylforamide) was mixed with 0.07 mmoles of dodecyl or octyl amine in 450 µl of 50:50 (v/v) acetone:50 mM sodium borate, 50 mM potassium chloride, $pH_{9.3}$ in a tape covered screw cap tube. After 15 min, 100 µl of additional 50:50 (v/v) acetone:50 mM sodium borate, 50 mM potassium chloride was added to the tube to produce the stock MDPF derivative solutions.

EXAMPLE 34

Staining of Gels with the Octyl and Dodecyl Derivatives of MDPF

A fifteen well, 12% gel was made as described in example 5 and was loaded with diluted Promega Mid Range Molecular Weight Standards to produce lanes containing samples having 200, 100, 80, 60, 40, 20 and 10 ng of protein per band. The gel was run as described in example 5 except that Promega Green 1 was not added to the cathode buffer. After electrophoresis, the gel was cut between lanes to produce gel segments containing fractionated protein samples at each of the concentrations listed above and these were placed in 30% methanol for 25–30 min at room temperature. The stock stain solutions of Example 33 were then diluted into distilled water at a concentration of 0.5% (v/v), and 50 ml of these solutions were used to stain the gels. After 1 hr incubation, the gels were visualized and photographed using a transilluminator. The gel containing the octyl MDPF derivative displayed stained fluorescent bands of the protein species to a concentration as low as 20 ng per band for most of the species fractionated from the standard mix. The gels were then placed in 5% methanol and allowed to destain overnight.

After overnight destaining, the gel segments were again placed upon a transilluminator, visualized and photographed. At this point, the dodecyl MDPF derivative stained gel displayed fluorescently stained protein species in the lanes to a concentration as low as 20 ng of protein per band. However, almost all of the fluorescent staining of the octyl MDPF derivative stained gel had been lost in the destaining protocol at this point. Nonetheless, these derivatives can be used for sensitive post-electrophoretic staining of proteins in gels.

EXAMPLE 35

In-gel Staining with the Octyl and Dodecyl Derivatives of MDPF

Two 10-well, 12% gels were made as described in Example 5 and were loaded with diluted Promega Mid Range Molecular Weight Standards to produce lanes containing 200, 100, 80, 60, 40, 20, 10, and 5 ng of protein per band following fractionation by electrophoresis. These protein levels were applied to the gels in 10 μl of loading buffer described in Example 5 and then 10 μl of a 1:100 dilution of the derivative stock solution (Example 33) into a solution of 20% glycerol, 1% sodium dodecyl sulfate was added to the wells. The gels were then run as described in Example 5 except that 0.5 ml of derivative stain stock was added to the cathode buffer in the gel and the Promega Green 1 dye was omitted from the solution. The gels were placed on a transilluminator following electrophoresis and were observed visually and photographed as described above. Staining of the protein bands was seen down to 80 ng of protein per band for the dodecyl derivative for all proteins and, for the 31 kdalton standard (carbonic anhydrase) down to 60 ng/band. Staining of the bands was seen to 60 ng/band for all proteins with the octyl derivative, with the carbonic anhydrase being detectable down to 40 ng per band. Therefore both stains can be used for in-gel staining of proteins.

EXAMPLE 36

Synthesis of Derivatives of Fluorescein Isothiocyanate

A stock solution of fluorescein isothiocyanate in acetone was prepared by dissolving 230 mg of the isothiocyanate (isomer I, Sigma Chemical Co., St. Louis, Miss., USA) in 12 ml of acetone. Two ml samples of this solution were placed in separate test tubes and 1 ml of 1:1 acetone:50 mM sodium borate, 50 mM potassium chloride, pH 9.3, containing potassium p-amino benzoate (17.5 mg/ml) (reaction 1); phenylenediamine (108 mg/ml)(reaction 2); or ethyl p-amino benzoate (16.5 mg/ml)(reaction 3) was added. Two additional reaction mixtures were prepared: one containing 4 ml of the fluorescein isothiocyanate stock and 1 ml of the phenylenediamine stock described above (reaction 4), the other containing 2 ml of the fluorescein stock and 1 ml of 1:1 acetone:50 mM sodium borate, 50 mM potassium chloride, $pH_{9.3}$ without any added reagent (reaction 5). Following overnight incubation at room temperature, 1 ml of 100 mM ammonium acetate, 500 mM Tris-HCl, pH 8.9, was added to the reactions. After an additional 4 hrs., ethanol was added to the solutions to 15 ml final volume to produce the stock solutions of derivatized dyes.

These reactions were defined as producing the following derivatives;

| REACTION NUMBER | DERIVATIVE |
| --- | --- |
| 1 | p-amino benzoic acid fluorescein |
| 2 | mixture of fluorescein phenylenediamine and difluorescein phenylenediamine |
| 3 | ethyl p-amino benzoic acid fluorescein |
| 4 | difluorescein phenylenediamine |
| 5 | amino fluorescein |

EXAMPLE 37

Use of Fluorescein Isothiocyanate Derivatives in Post-Electrophoretic Staining of Proteins Fractionated in Gels Six 12% gels were made as described in Example 27 and were loaded with diluted Promega Mid Range Molecular Weight standard to produce lanes containing, per band, 1000, 500, 200, 100, 75, 50, 25 and 10 ng of protein. The gel was run as described in Example 27 and then the gels were incubated 15 min in 50% methanol. The gels were then transferred to individual 50 ml staining solutions, which were stock derivatized dye solutions of Example 36 diluted 1:500 with 10% methanol. After one hour, these solutions were removed and destaining with 50 ml of 10% methanol was performed. After an additional 30 min. the gels were visualized on a transilluminator and photographed. Protein bands were visible for the gels stained with amino fluorescein and p-amino benzoic acid fluorescein derivatives, however the bands were seen only in the lanes containing 1000, 500, and 200 ng of protein per band. In addition, the amino derivative only allowed detection of the 97, 66, 55 and 40 kDa (kilodalton) standards and the p-amino benzoyl derivative only the 97, 55, 40 and 31 kDa standards. At this point, the gel stained with the ethyl p-amino benzoyl derivative allowed detection of all of the proteins in the lanes containing as little as 75 ng of protein per band.

The gels were then placed in 50 ml of 10% methanol and allowed to incubate overnight at room temperature. After overnight incubation, the gels were visualized on a transilluminator and photographed. At this point, the gels stained with the difluorescein phenylenediamine, ethyl p-amino benzoyl, and p-amino benzoyl derivatives showed staining of all protein species in the lanes containing 1000, 500, and 200 ng of protein per band. The gel stained with the amino derivative (reaction 5) had faded to the point where protein species were only detected in the 1000 and 500 ng protein per band lanes. However, in these lanes, only particular protein species were stained, as described above. These results indicate that the derivatization of fluorescein isothiocyanate with various hydrophobic, organic reagents allows the resulting compounds to have an increased binding affinity for denatured protein, thus allowing an improved detection sensitivity for denatured protein in comparison with the amino derivative, which is also, like the organic-reagent-derivatized, incapable of binding covalently with protein.

EXAMPLE 38

Synthesis of Dodecyl and Octyl Amine Derivatives of Fluorescein Isothiocyanate

Fluorescein isothiocyanate (isomer I, Sigma Chemical Co.), 18 mg, in 450 μl of dimethyl formamide was mixed with 0.05 mmole of either octyl or dodecyl amine added as a suspension in a 1:1 mixture of acetone:50 mM sodium borate, 50 mM potassium chloride, pH 9.3. Stock stain solutions were then made by diluting the reaction mixtures to 1 ml by addition of the acetone, sodium borate, potassium chloride solution described above. These stock solutions were held at room temperature before use.

EXAMPLE 39

Use of Dodecylamino and Octylamino Derivatives of Fluorescein Isothiocyanate in the Detection of Denatured Protein Gels were made and loaded as described in Example 34. The gels were incubated in 30% methanol for 15 min to fix the protein and then were incubated in 50 ml of a solution of the stains of Example 38 made by dilution of the stock stain solutions described in Example 38 to a concentration of 0.5% (v/v) in distilled water. After incubation in the staining solution for 1 hr, the gels were placed in 5% methanol and were visualized and photographed after 30 min by placement of the gel segment on a transilluminator. Photography of the segments was performed as described in Example 27. At this point, protein bands were visualized in the gel stained with the dodecylamino derivative at a concentration as low as 80 ng of protein per band. The gel stained with the octylamino derivative had a high background fluorescence which prevented visualization of the protein bands.

The gel segments were then returned to the destaining solutions and allowed to incubate overnight. The segment of the gel stained with the octylamino derivative was transferred to a solution of 30% methanol following the overnight incubation and was revisualized and rephotographed after 1 hr of incubation in this methanol solution. At this point, protein was detected at fluorescently labeled bands to a concentration as low as 40 ng of protein per band. These data, taken with those of Examples 37 and 38, indicate that the modification of the stain by addition of linear hydrocarbon side-chains does improve the ability of the resulting materials to bind non-covalently to proteins.

EXAMPLE 40

Synthesis of NBODY Derivatives

Succinimidyl-6-(7-nitrobenz-2-oxa-1,3-diazol-4-yl) amino hexanoate, 25 mg (available from Molecular Probes, Eugene, Oregon, Stock number S1167) (referred to hereinafter as "Succinimidyl NBODY") was dissolved in 2.5 ml of ethanol. The reagents n-dodecyl amine and n-hexadecyl amine were dissolved to 9 and 12 mg/ml in ethanol, respectively. A reaction buffer was prepared by making a solution of 200 mM sodium borate pH 9.0 by placing sufficient boric acid to produce a 200 mM solution in 90% of the water needed to make the solution and adding solid sodium hydroxide to adjust the pH of the solution to pH 9.0 and then diluting the solution to the final volume needed to adjust the borate concentration to 200 mM. The following reaction mixtures were prepared: control reaction mixture: 1 ml ethanol, 0.5 ml reaction buffer, and 3 ml of water were mixed and after mixing, 0.5 ml of the Succinimidyl NBODY solution was added; NBODY-C12 reaction mixture: 1 ml of reaction buffer, 6 ml of water and 2 ml of dodecyl amine were mixed, the reaction was then initiated by addition of 1 ml of the Succinimidyl NBODY solution to this mixture followed by mixing by vortexing; NBODY-C16 reaction mixture: 1 ml of reaction buffer, 6 ml water, 2 ml hexadecyl amine solution were mixed, the reaction was then initiated by addition of 1 ml of Succinimidyl NBODY solution to this mixture followed by mixing by vortexing. After about 5 min. the NBODY-C12 and the NBODY-C16 reaction mixtures formed a gel. In order to dissolve these gels and to keep the same relative ratio of reagents in the control and amine containing reaction mixtures, 1.5 ml of ethanol were added to the control reaction mixture and 3.0 ml of ethanol were added to each of the amine-containing reaction mixtures. After 30 min., 0.5 microliter samples of the three reaction mixtures were spotted on a silica gel TCL plate and the plate was developed using a 6:1 ratio of tolulene:ethyl acetate. Following development, the plate was observed on a transilluminator. Each of the aliquots of the reaction mixtures which contained the amines showed the presence of a new fluorescent species not present in the aliquot of the control reaction mixture.

EXAMPLE 41

Detection of Protein Post-Electrophoretically Using NBODY Derivatives

Promega Mid-Range Molecular Weight Standards were diluted and heated as described in Example 27 to produce solutions containing 125, 25, 5 and 1 ng of protein per band in 10 microliters of solution. A 10% Tris Glycine, precast polyacrylamid gel from Novex Corp. (San Diego, Calif., USA, Cat. No. EC 6075.) was loaded with 10 microliters of the just described, diluted molecular weight standard solutions in lanes so that two lanes, each with the same diluted standard solution, were separated by a blank lane. The gel was developed using conditions recommended by the manufacturer and following development, the gel was cut in the blank lane. The segments were placed in 50 ml of 5% acetic acid, 20% ethanol. Six hundred microliters of the NBODY-C12 reaction mixture from Example 40 was added to the solution with one of the segments of a pair (of lanes with the same protein molecular weight standard solution) and three hundred microliters of the NBODY-C16 reaction mixture from Example 40 was added to the solution with the other segment of the same pair. After one hour of incubation, the gel segments were photographed on a transilluminator as described in example 27. Protein bands were detected in the lanes containing the 125 and 25 ng of protein per band using this method and the crude dye solutions from Example 40.

EXAMPLE 42

Sensitive Post-Electrophoretic Detection of Protein Using a NBODY Dye

A 12% SDS-PAGE gel was prepared as described in Example 27 and was loaded with dilute Promega Mid-Range Molecular Weight Markers (diluted and heated as in Example 27) to produce lanes which contained 100, 80, 60, 40, 20, 10 and 5 ng of protein per band. The gel was run in a BioRad Miniprotean II gel system at 50V for 1.5 hr. then 125V until the tracking dye reached the bottom of the gel. After the dye reached the bottom of the gel, the gel was removed from the apparatus and placed in 50 ml of 5% acetic acid, 20% ethanol.

The NBODY dye prepared as in Example 40 with n-dodecyl amine was purified by applying 2 ml of the NBODY-C12 reaction mixture from Example 40 3cm from one edge of a 25×25cm silica gel plate (Sigma Chemical Co., St. Louis, Miss., USA). The plate was developed using a 6:1 ratio of tolulene:ethyl acetate. The silica gel region containing the dye (with high relative mobility) was scrapped from the plate and the dye was released by placing this silica gel in 50 ml of ethanol. This solution in 50 ml ethanol is the purified NBODY-C12 solution used below.

After 30 minutes in the 5% acetic acid, 20 % ethanol, the gel was removed from that solution and replaced with a solution containing the purified NBODY-C12 stain with the following composition: one ml of purified NBODY-C12 solution was placed in 50 ml of 35% ethanol, 5% acetic acid. After one hour, the dye solution was removed and was replaced with 50 ml of water. After one hour in the water solution, the gel was scanned on a Molecular Dynamics Fluoroimager (Molecular Dynamics, Sunnyvale, Calif.), which excites fluorescence with laser light of 483 nm wavelength. Protein bands were seen for all of the protein species in the lanes containing all protein concentrations. This indicates that the detection limit for the NBODY derivative made with n-dodecyl amine in the solution and under the conditions described here is lower than 5 ng of protein when the protein is fractionated under the conditions described in this Example.

It is to be understood that the invention is not limited to the particular embodiments specifically dis- closed herein, but embraces such modified forms thereof as come within the scope of the following claims.

We claim:

1. A dye of Formula of XCI

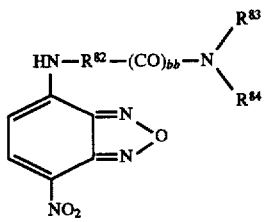

wherein $R^{82}$ is —$(CH_2)_n$—, n having the value of 1–20, bb is 1, $R^{83}$ is hydrogen or alkyl of 1–20 carbons, phenyl, or benzyl, and $R^{84}$ is, independently of $R^{83}$, hydrogen, alkyl of 1–20 carbons, phenyl or benzyl, provided that at least one of $R^{83}$ and $R^{84}$ is other than hydrogen, or a salt thereof.

2. A dye of claim 1 wherein bb is 1, $R^{82}$ is —$(CH_2)_5$—, one of $R^{83}$ and $R^{84}$ is hydrogen and the other of $R^{83}$ and $R^{84}$ is selected from the group consisting of n-dodecyl and n-hexadecyl.

3. A method of detecting a protein which comprises (A) making a complex of the protein with a dye of Formula XCI

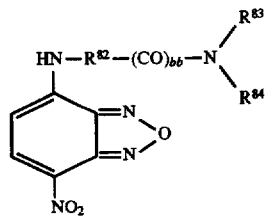

wherein $R^{82}$ is —$(CH_2)_n$—, n having the value of 1–20, bb is 0 or 1, $R^{83}$ is hydrogen or alkyl of 1–20 carbons, phenyl, or benzyl, and $R^{84}$ is, independently of $R^{83}$, hydrogen, alkyl of 1–20 carbons, phenyl or benzyl, provided that at least one of $R^{83}$ and $R^{84}$ is other than hydrogen, and (B) detecting the complex by observing the color or the fluorescence of the complex due to the presence of the dye of Formula XCI in the complex.

4. A method of detecting protein in a sample comprising the steps of:

(a) applying a sample solution comprising a protein to a polyacrylamide or agarose gel;

(b) separating the sample into protein fractions using electrophoresis;

(c) staining the protein on the support with a dye of Formula XCI

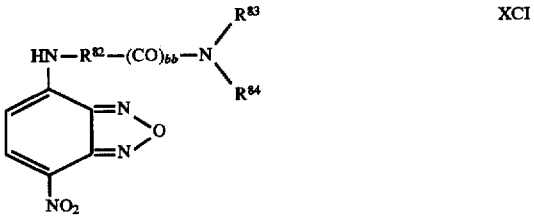

wherein $R^{82}$ is —$(CH_2)_n$—, n having the value of 1–20, bb is 0 or 1, $R^{83}$ is hydrogen or alkyl of 1–20 carbons, phenyl, or benzyl, and $R^{84}$ is, independently of $R^{83}$, hydrogen, alkyl of 1–20 carbons, phenyl or benzyl, provided that at least one of $R^{83}$ and $R^{84}$ is other than hydrogen, and (d) detecting the stained protein by observing the fluorescence of the complex due to the presence of the dye of Formula XCI in the complex.

5. A method according to claim 3 wherein, in the compound of Formula XCI, bb is 1, $R^{82}$ is —$(CH_2)_5$—, one of $R^{83}$ and $R^{84}$ is hydrogen, and the other of $R^{83}$ and $R^{84}$ is selected from the group consisting of n-dodecyl and n-hexadecyl.

6. A method according to claim 4 wherein, in the compound of Formula XCI, bb is 1, $R^{82}$ is $(CH_2)_5$—, one of $R^{83}$ and $R^{84}$ is hydrogen, and the other of $R^{83}$ and $R^{84}$ is selected from the group consisting of n-dodecyl and n-hexadecyl.

* * * * *

UNITED STATES PATENT AND TRADEMARK OFFICE
CERTIFICATE OF CORRECTION

PATENT NO. : 5,705,649
DATED : January 6, 1998
INVENTOR(S) : John W. Schultz; David L. Leland It is certified that error appears in the above-identified patent and that said Letters Patent is hereby corrected as shown below:

Column 8, line 21 of the patent, insert the word --is-- after the word --and--.

Column 14, line 55 of the patent, delete "(i)" in the formula and insert in its place --(ii)--.

Column 14, line 62 of the patent, delete "(ii)" in the formula and insert in its place --(iii)--.

Column 17, line 51 of the patent, delete "X11" and insert in its place --$X_{11}$--.

Column 18, line 48 of the patent, delete "bromo chloro cyano" and insert in its place --bromo, chloro, cyano--.

Column 22, line 65 of the patent, delete "$(S_{12})—(D_3)$" and insert in its place --$(X_{12})—(D_3)$--.

Column 34, line 19 of the patent, delete "i" and insert in its place --1--.

Column 34, line 60 of the patent, delete "pHS.8" and insert in its place --pH8.8--.

Column 35, line 13 of the patent, delete "i" and insert in its place --1--.

UNITED STATES PATENT AND TRADEMARK OFFICE
CERTIFICATE OF CORRECTION

PATENT NO. : 5,705,649
DATED : January 6, 1998
INVENTOR(S) : John W. Schultz; David L. Leland It is certified that error appears in the above-identified patent and that said Letters Patent is hereby corrected as shown below:

Column 38, line 52 of the patent, delete "0.0156g" and insert in its place --0.0156µg--.

Column 38, line 62 of the patent, delete "i" and insert in its place --1--.

Column 39, line 67 of the patent, delete "636" and insert in its place --630--.

Column 40, line 45 of the patent, delete "run" and insert in its place --nm--.

Column 45, line 30 of the patent, delete "i" and insert in its place --1--.

Column 50, line 22 of the patent, delete "$pH_{9.3}$" and insert in its place --pH 9.3--.

UNITED STATES PATENT AND TRADEMARK OFFICE
CERTIFICATE OF CORRECTION

PATENT NO. : 5,705,649
DATED : January 6, 1998
INVENTOR(S) : John W. Schultz; David L. Leland It is certified that error appears in the above-identified patent and that said Letters Patent is hereby corrected as shown below:

Column 51, line 40 of the patent, delete "pH9.3" and insert in its place --pH 9.3-.

Column 56, line 35 of the patent, insert delete "(CH2)5" and insert in its place-- -(CH2)5--.

Signed and Sealed this

Twenty-fifth Day of May, 1999

Attest:

Q. TODD DICKINSON

Attesting Officer

Acting Commissioner of Patents and Trademarks